United States Patent
Schell

(10) Patent No.: US 7,918,121 B2
(45) Date of Patent: *Apr. 5, 2011

(54) METER SYSTEM DESIGNED TO RUN SINGULATED TEST SENSORS

(75) Inventor: Robert D. Schell, Goshen, IN (US)

(73) Assignee: Bayer Healthcare, LLC, Tarrytown, NY (US)

( * ) Notice: Subject to any disclaimer, the term of this patent is extended or adjusted under 35 U.S.C. 154(b) by 687 days.

This patent is subject to a terminal disclaimer.

(21) Appl. No.: 11/890,626

(22) Filed: Aug. 7, 2007

(65) Prior Publication Data

US 2008/0034834 A1 Feb. 14, 2008

Related U.S. Application Data

(60) Provisional application No. 60/837,518, filed on Aug. 14, 2006.

(51) Int. Cl.
*G01N 21/00* (2006.01)

(52) U.S. Cl. .......................................... 73/1.02

(58) Field of Classification Search .................. None
See application file for complete search history.

(56) References Cited

U.S. PATENT DOCUMENTS

| | | | |
|---|---|---|---|
| 4,481,804 A * | 11/1984 | Eberhard et al. ............... | 73/1.06 |
| 5,597,532 A | 1/1997 | Connolly ......................... | 422/58 |
| 5,628,890 A | 5/1997 | Carter et al. .................... | 204/403 |
| 5,630,986 A | 5/1997 | Charlton et al. ................. | 422/64 |
| 5,700,695 A | 12/1997 | Yassinzadeh et al. ......... | 436/180 |
| 5,856,195 A | 1/1999 | Charlton et al. | |
| 5,989,917 A * | 11/1999 | McAleer et al. ................ | 436/46 |
| 2007/0212258 A1 | 9/2007 | Neel et al. | |
| 2007/0293790 A1 | 12/2007 | Bainczyk et al. .............. | 600/583 |
| 2008/0033271 A1* | 2/2008 | Say et al. ........................ | 600/347 |
| 2008/0034835 A1* | 2/2008 | Schell ............................ | 73/1.02 |

FOREIGN PATENT DOCUMENTS

| | | |
|---|---|---|
| DE | 102004062255 B3 | 2/2006 |
| DE | 102004057503 A1 | 6/2006 |
| EP | 0 732 590 A2 | 9/1996 |
| EP | 0 840 122 A2 | 5/1998 |
| EP | 1 398 631 A2 | 3/2004 |
| WO | WO 2004/113911 A1 | 12/2004 |
| WO | WO 2005/040793 | 5/2005 |
| WO | WO 2006/069675 | 7/2006 |

OTHER PUBLICATIONS

Written Opinion corresponding to International Patent Application Serial No. PCT/US2007/017691, European Patent Office, dated Apr. 28, 2008, 6 pages.

International Search Report corresponding to International Patent Application Serial No. PCT/US2007,017691, European Patent Office, dated Apr. 28, 2008, 6 pages.

* cited by examiner

*Primary Examiner* — Robert R Raevis
(74) *Attorney, Agent, or Firm* — Nixon Peabody LLP

(57) ABSTRACT

A test system comprises a sensor container and a testing device. The sensor container has a base and a lid. The container encloses a plurality of test sensors therein. The container includes a calibration label attached thereto. The label includes electrical contacts located thereon that encode calibration information onto the calibration label. The testing device has a sensor-container opening formed thereon. The sensor-container opening has an auto-calibration feature located therein. The auto-calibration feature is external to the testing device. The auto-calibration feature includes calibration elements to communicate with the electrical contacts on the calibration label. The testing device determines the calibration information encoded on the calibration label in response to the calibration elements engaging the electrical contacts. A portion of the sensor container remains external to the meter while the encoded calibration information is being determined.

22 Claims, 28 Drawing Sheets

| CONTACT | SET |
|---|---|
| A | INNER OR OUTER |
| B | INNER OR OUTER |
| C | INNER OR OUTER |
| D | INNER OR OUTER |
| E | INNER OR OUTER |
| F | INNER OR OUTER |
| G | INNER OR OUTER |
| H | INNER OR OUTER |
| I | OUTER |
| J | SYNC |

| CONTACT | TYPE 1 | TYPE 2 | TYPE 3 | TYPE 4 |
|---|---|---|---|---|
| A | SYNC 2 | INNER OR OUTER | INNER OR OUTER | INNER OR OUTER |
| B | INNER OR OUTER | SYNC 2 | INNER OR OUTER | INNER OR OUTER |
| C | INNER OR OUTER | INNER OR OUTER | SYNC 2 | INNER OR OUTER |
| D | INNER OR OUTER | INNER OR OUTER | INNER OR OUTER | SYNC 2 |
| E | INNER OR OUTER | INNER OR OUTER | INNER OR OUTER | INNER OR OUTER |
| F | INNER OR OUTER | INNER OR OUTER | INNER OR OUTER | INNER OR OUTER |
| G | INNER OR OUTER | INNER OR OUTER | INNER OR OUTER | INNER OR OUTER |
| H | INNER OR OUTER | INNER OR OUTER | INNER OR OUTER | INNER OR OUTER |
| I | OUTER | OUTER | OUTER | OUTER |
| J | SYNC 1 | SYNC 1 | SYNC 1 | SYNC 1 |

Fig. 6e

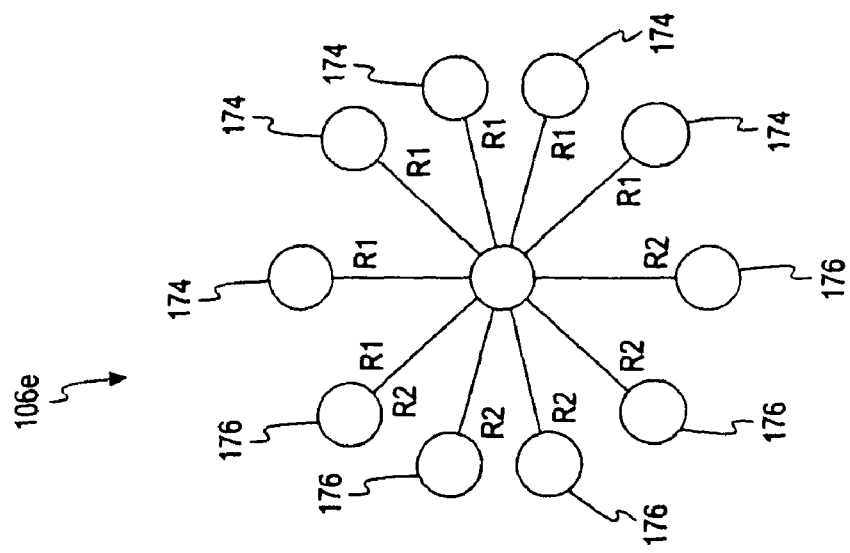
Fig. 7d
Fig. 7c
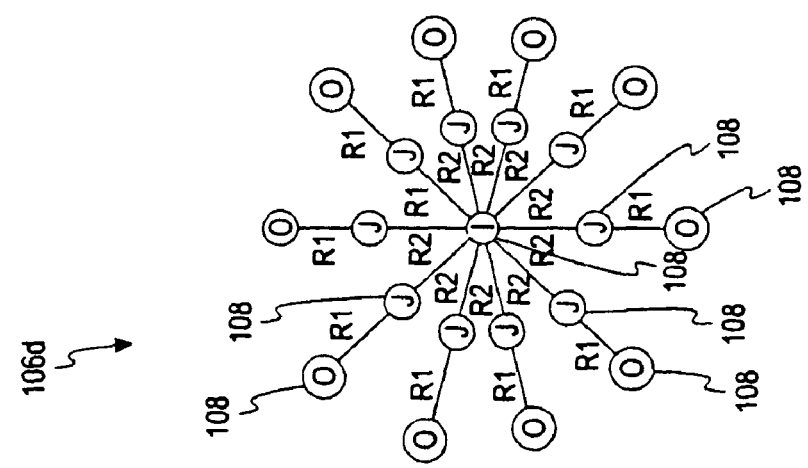
Fig. 7b

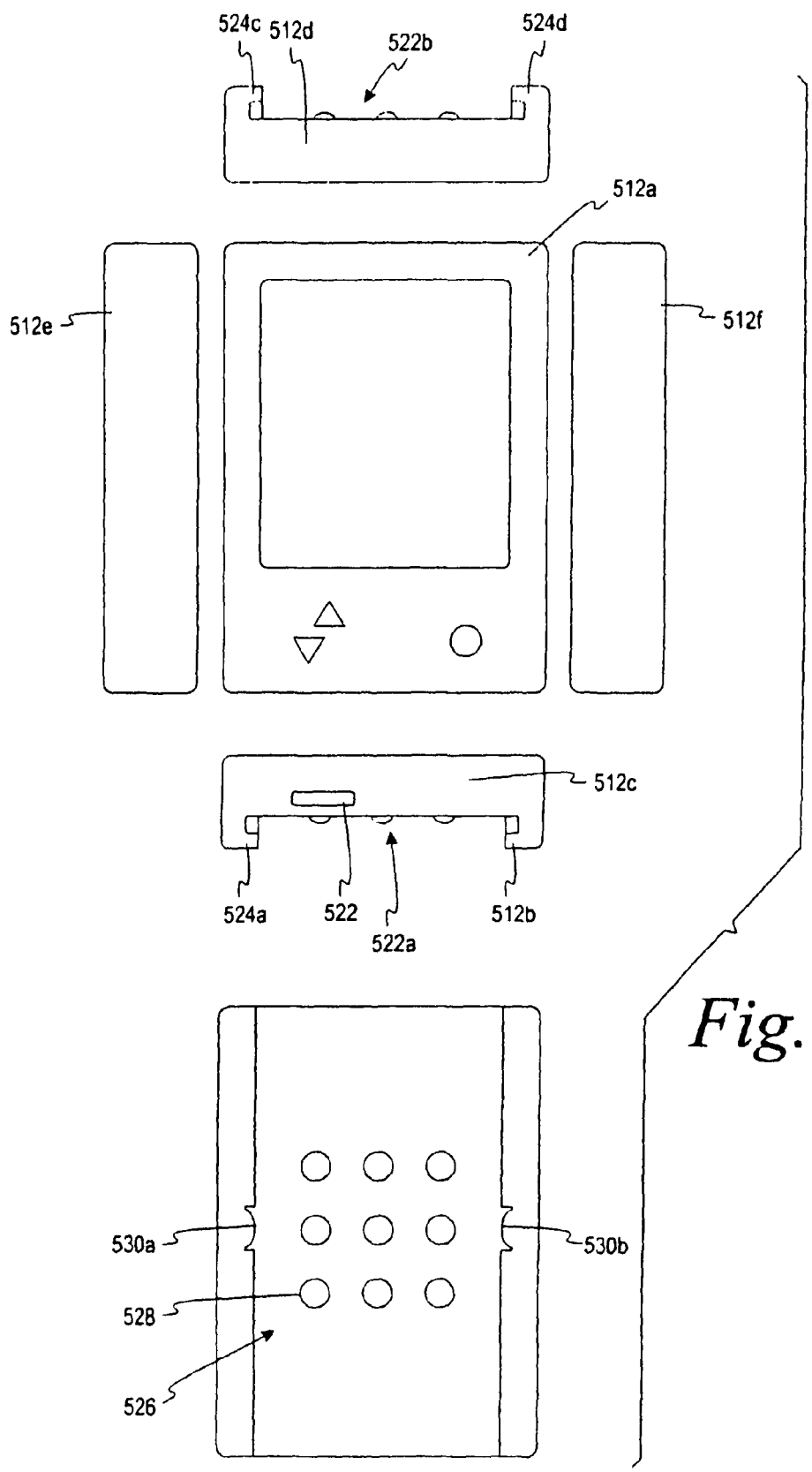

METER SYSTEM DESIGNED TO RUN SINGULATED TEST SENSORS

CROSS REFERENCE TO RELATED APPLICATION

This application claims priority to Application No. 60/837,518 filed on Aug. 14, 2006, which is incorporated by reference in its entirety.

FIELD OF THE INVENTION

The present invention relates generally to an auto-calibration label used to automatically calibrate instruments or meters that determine the concentration of an analyte. The auto-calibration labels are incorporated onto a package of singulated test strips and an external portion of the instrument or meter is adapted to determine the calibration information from the label when the package is attached to the meter.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently monitor the glucose level in their body fluids in order to manage its level. The results of such tests can be used to determine what, if any, insulin or other medication needs to be administered. In one type of blood-glucose testing system, sensors are used to test a sample of blood.

A test sensor contains biosensing or reagent material that reacts with blood glucose. In some mechanisms, the testing end of the sensor is adapted to be placed into the fluid being tested, for example, blood that has accumulated on a person's finger after the finger has been lanced. The fluid is drawn into a capillary channel that extends in the sensor from the testing end to the reagent material by capillary action so that a sufficient amount of fluid to be tested is drawn into the sensor. The fluid then chemically reacts with the reagent material in the sensor resulting in an electrical signal indicative of the glucose level in the fluid being tested. This signal is supplied to the meter via contact areas located near the rear or contact end of the sensor and becomes the measured output. In other mechanisms, the sensor has a reagent area upon which the blood is applied. The resulting chemical reaction produces a color change. When the sensor is inserted into an instrument, the color change can be optically measured and converted into an equivalent glucose concentration value.

Diagnostic systems, such as blood-glucose testing systems, typically calculate the actual glucose value based on a measured output and the known reactivity of the reagent-sensing element (test sensor) used to perform the test. The reactivity or lot-calibration information of the test sensor may be given to the user in several forms including a number or character that they enter into the instrument. Another method for calibrating strips contained within a package is to include a calibration chip within the sensor packaging that is inserted into the test instrument. When plugged into the instrument, the calibration chip's memory element is electrically coupled to the instrument's microprocessor board for directly reading the stored calibration information by the instrument.

These methods suffer from the disadvantage of relying on the user to properly enter the calibration information, which some users may not enter at all or may input incorrectly. In this event, the test sensor may use the wrong calibration information and thus return an erroneous result. Where a calibration chip is contained within the sensor packaging, the calibration chip can be easily lost or misplaced, resulting in an inability to enter the sensor information via the calibration chip.

Improved systems use an auto-calibration label that is affixed to a sensor cartridge. The auto-calibration label is read automatically when the cartridge is loaded into the meter and requires no additional user intervention. However, such an auto-calibration method requires a cartridge that can be loaded into the meter, that can provide environmental protection for long-term stability of the stored sensors, and that it can provide automated access to the sensors. Simpler forms of such a cartridge, where sensors are sealed in individual compartments, generally provide little or no flexibility to vary the number of sensors that can packaged and the maximum is limited by the maximum acceptable cartridge size. Cartridges with sensors stacked within a common compartment can support larger and potentially variable numbers of stored sensors, but providing a good environmental seal after the first sensor is extracted is difficult, has associated technical complexity and costs associated with automated sensor access, and, in simpler forms, may be inflexible in the number of sensors that can be packaged.

It would be desirable to provide a device and method that provides the lot calibration information of the test sensor to instruments or meters in a reliable manner without the complexity, cost, and constraints of an automated cartridge, without the need for manual entry of calibration information by the user, and without the need for a separate calibration chip that can be lost. This is particularly desirable for systems designed to work with individual sensors packaged in a bottle or other container that is separate from the instrument and flexible in the number of sensors that can be packaged rather than in a specialized cartridge that is loaded into the instrument for automatic sensor dispensing.

SUMMARY OF THE INVENTION

According to one embodiment of the present invention, a test system for determining an analyte concentration in a fluid sample is disclosed. The test system comprises a sensor container and a testing device. The sensor container has a base and a lid and is adapted to enclose a plurality of test sensors therein. The sensor container includes a calibration label attached thereto. The calibration label includes a plurality of electrical contacts located thereon. The electrical contacts are adapted to encode calibration information onto the calibration label. The testing device has a sensor-container opening formed thereon. The sensor-container opening has an auto-calibration feature located therein. The auto-calibration feature is external to the testing device. The auto-calibration feature includes a plurality of calibration elements being adapted to communicate with the plurality of electrical contacts on the calibration label. The testing device is adapted to determine the calibration information encoded on the calibration label in response to the calibration elements engaging the electrical contacts. A portion of the sensor container remains external to the meter while the encoded calibration information is being determined.

According to another embodiment of the present invention, a test system for determining an analyte concentration in a fluid sample is disclosed. The test system comprises a sensor and a testing device. The sensor container has a base and a lid. The sensor container includes a calibration label attached thereto. The calibration label includes a plurality of electrical contacts located thereon. A first one of the plurality of electrical contacts is connected via a conductive trace to a first ring, a second one of the plurality of electrical contacts is connected via a conductive trace to a second ring, and a third one of the plurality of electrical contacts is disconnected from both the first and second ring. The calibration information is encoded onto the calibration label based on the connections and disconnections of the electrical contacts with the first and second ring. The testing device has a microprocessor internally located therein and a sensor-container opening formed thereon. The sensor-container opening has an auto-calibration feature located therein. The auto-calibration feature is external to the testing device and includes a plurality of calibration elements being adapted to communicate with the plurality of electrical contacts on the calibration label. The microprocessor is adapted to determine the calibration information encoded on the calibration label in response to the plurality of electrical contacts engaging the plurality of calibration elements external to the testing device.

The above summary of the present invention is not intended to represent each embodiment, or every aspect, of the present invention. Additional features and benefits of the present invention are apparent from the detailed description and figures set forth below.

BRIEF DESCRIPTION OF THE DRAWINGS

FIG. 1b is an opposing side view of the integrated meter of FIG. 1a.

FIG. 6e is a chart illustrating digital auto-calibration encoding labels, in accordance with FIG. 6d.

FIG. 7b is an expanded view of alternative analog auto-calibration encoding label useful in the present invention.

FIG. 7c is an expanded view of alternative analog auto-calibration encoding label useful in the present invention.

FIG. 7d is a chart illustrating further alternative analog auto-calibration encoding labels in accordance with the present invention.

FIG. 13a is a layout view of a meter adapted to seat a sensor container, according to another embodiment of the present invention.

FIG. 13c is a layout view of the sensor cartridge of FIG. 13b seated, in a first position, on the meter of FIG. 13a.

FIG. 13d is a layout view of the sensor cartridge of FIG. 13b seated, in a second position, on the meter of FIG. 13a.

DESCRIPTION OF ILLUSTRATED EMBODIMENTS

An instrument or meter in one embodiment uses a test sensor adapted to receive a fluid sample to be analyzed, and a processor adapted to perform a predefined test sequence for measuring a predefined parameter value. The test sensor is removed from a sensor container prior to inserting the test sensor into the meter. A memory device is coupled to the processor for storing predefined parameter data values. Calibration information associated with the test sensor may be read by the processor before the fluid sample to be measured is received. Calibration information may be read by the processor before or after the fluid sample to be measured is received, but not after the concentration of the analyte has been determined. Calibration information is used in measuring the predefined parameter data value to compensate for different characteristics of test sensors, which will vary on a batch-to-batch basis. The calibration information is included on a calibration label on the exterior of the sensor container and is determined by an auto-calibration feature located on an external portion of the meter.

Figure 1A:
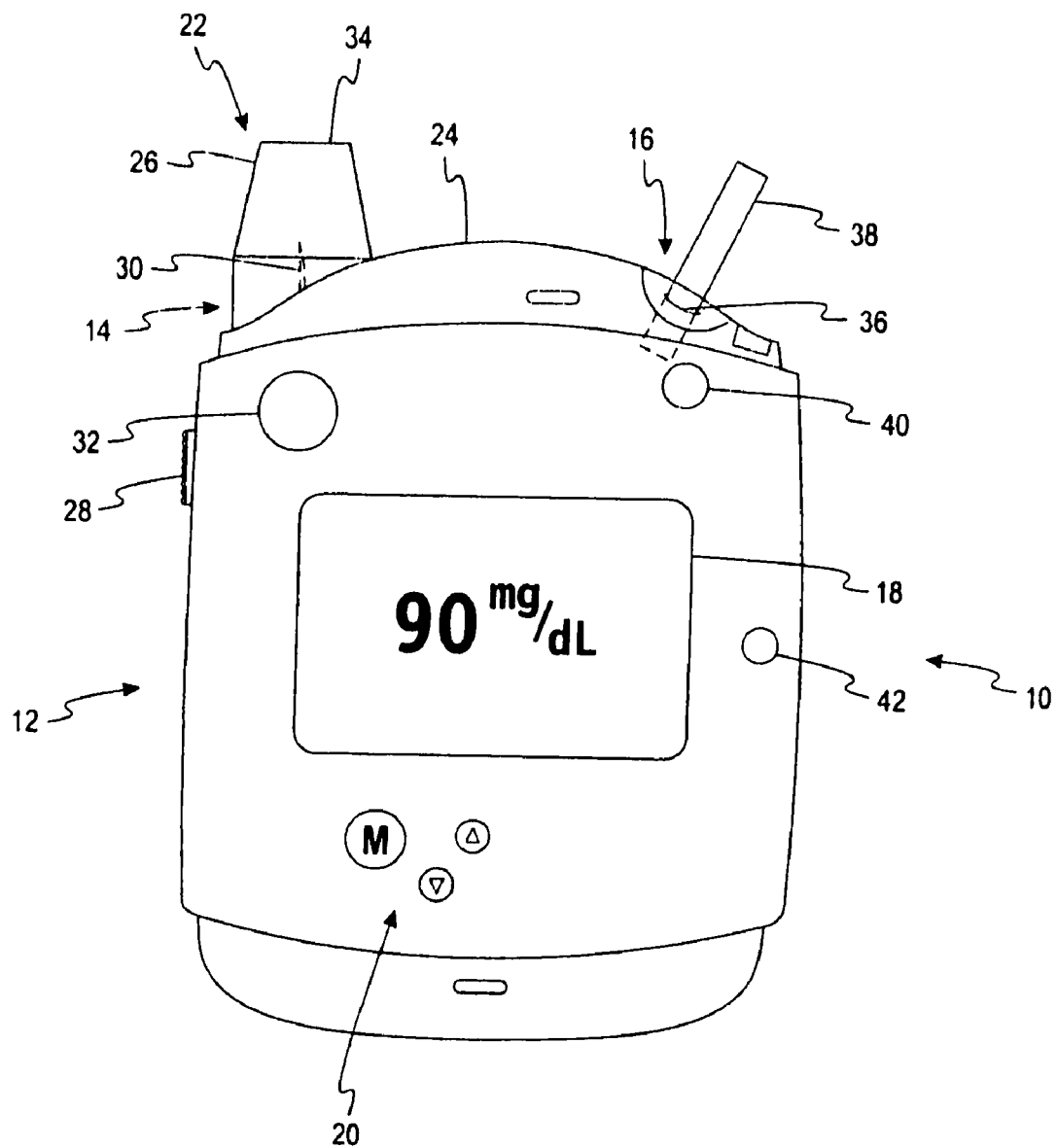
FIG. 1a is a side view of an integrated meter, according to one embodiment of the present invention.
Figure 1B:
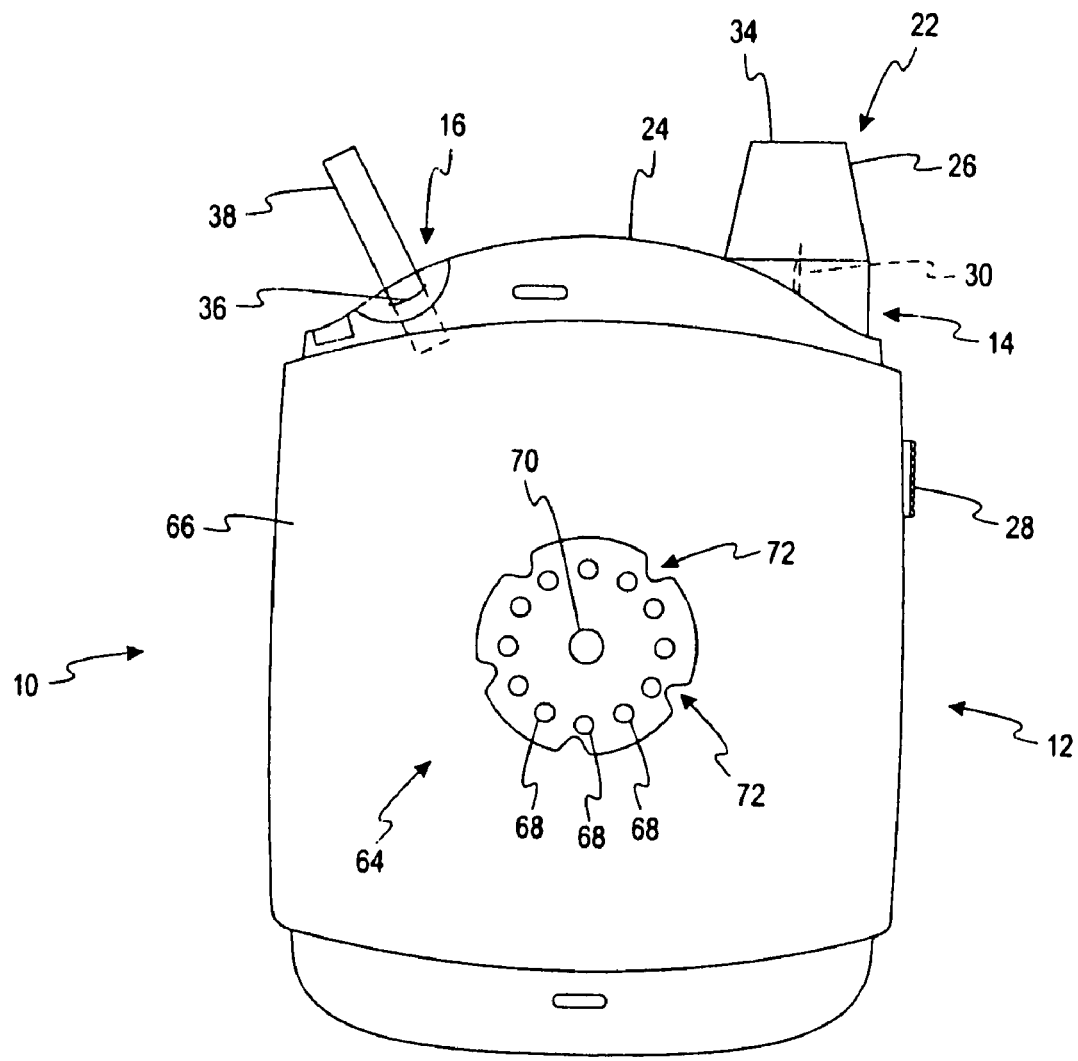

Turning now to the drawings and initially to FIGS. 1a-b, an integrated meter 10 is illustrated that may be used in combination with the present invention. The integrated meter 10 comprises a housing 12, a lancing mechanism 14, a testing mechanism 16, a display 18, and a button set 20. It should be noted that the integrated meter 10 is illustrated as an example of one particular instrument or meter that is adapted to be utilized with the present invention, however, other instruments, meters, or testing devices capable of performing an analysis on a fluid sample may also be adapted for use with the present invention.

The display 18 is used to display the determined concentration and provide other information to the test subject. The test subject may interact with the integrated meter 10 by utilizing the button set 20. An external portion 22 of the lancing mechanism 14 is located on a testing end 24 of the housing 12. The lancing mechanism 14 is partially enclosed within the housing 12 with a lancing endcap 26 removably attached to the external portion 22 of the lancing mechanism 14 opposite the housing 12. A slider 28 is located on the exterior of the housing 12 and is operatively connected to the lancing mechanism 14 so as to cock the lancing mechanism 14.

The lancing mechanism 14 is used to lance the skin of a test subject with a removably attached lance 30 (e.g., a lancet). The lancing endcap 26 has a central aperture and protects the test subject from inadvertently contacting the lance 30 located therein. The lance 30 is adapted to obtain a fluid sample from the test subject. In use, the slider 28 is utilized to cock the lancing mechanism 14—moving the lance 30 further into the housing 12. A firing button 32 is provided on the exterior of the housing 12 that, when depressed, fires the cocked lancing device 14. A face 34 of the endcap 26 can be touched to the skin of the test subject. The lancing device 14 can then be fired (by depressing the firing button 32) causing the lance 30 to extend from the endcap 26 and pierce the skin of the test subject. The lancing mechanism 14 is adjacent to the testing mechanism 16 for convenient side-by-side lancing and testing that reduces the required level of component manipulation by the user. As illustrated in FIG. 1, the testing mechanism 16 is angularly aligned on the meter 10 to facilitate an alternative site test when desirable. However, the location and interaction of the components of the integrated meter 10 may vary and a more detailed description of the various configurations is not necessary to understand the present invention.

The testing mechanism 16 includes a test-sensor opening 36 formed in the testing end 24 of the housing 12. The test-sensor opening 36 is adapted to seat a test sensor 38 therein. The test sensor 38 contains at least one reagent located thereon that is adapted to react with an analyte of interest within a fluid sample. The test sensor 38 may be seated in the test-sensor opening 36 by the test subject. Once seated, the test sensor 38 is connected to electrical circuitry 80 (FIG. 4) within the integrated meter 10 that is adapted to perform an electrochemical determination of the concentration of an analyte in a fluid sample. Alternatively, an optical read-head can be connected to the electrical circuitry of the integrated meter and an optical test sensor can be inserted near the optical read-head to allow for an analyte concentration of a fluid sample to be optically determined. An ejection mechanism 40 is provided to allow the test subject to remove the test sensor 38 from the integrated meter 10 once the fluid sample analysis has been performed.

Figure 5:
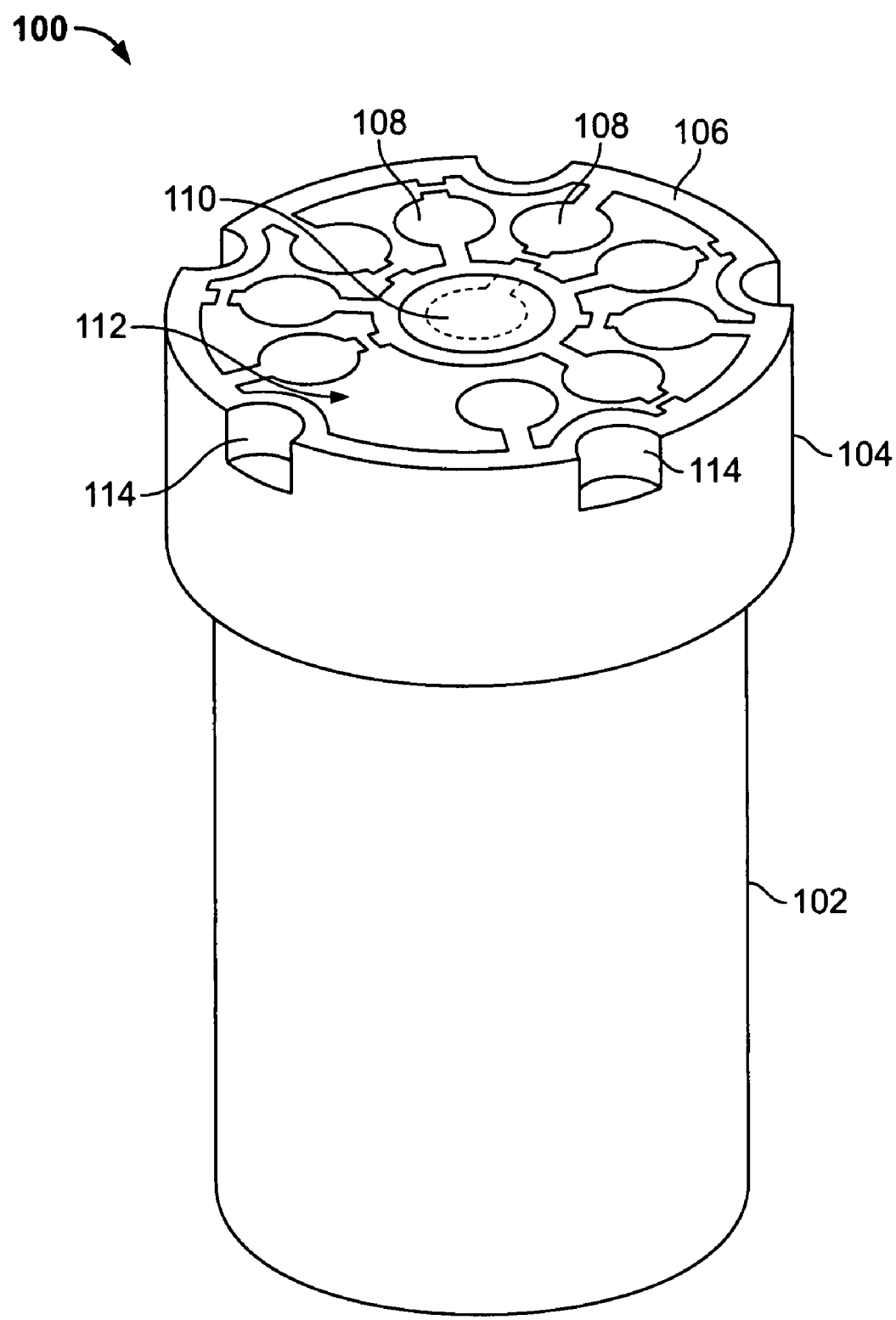
FIG. 5 is a sensor container that is adapted to contain a plurality of the electrochemical sensors, according to some embodiments of the present invention.

The integrated meter 10 includes an auto-calibration feature 64 (see FIG. 1b) on an exterior portion 66 of the housing 12. The auto-calibration feature 64 is adapted to interact with a calibration label 106 (illustrated in FIGS. 5-9 below) located on a sensor container 100 (FIG. 5). The auto-calibration feature 64 includes a plurality of calibration elements, such as calibration pins 68 that extend slightly from a portion of the auto-calibration feature 64. Such calibration pins 68 may be spring loaded to assure reliable connection and, should connection require sliding the calibration label 106 into place across the contacts, such calibration pins 68 may be tapered or rounded to reduce interference. Though the illustrated embodiment shows ten calibration pins 68 included within the auto-calibration feature 64 that are arranged substantially in a circular arrangement, it should be noted that the number of auto-calibration pins may vary in number and shape from those shown in FIG. 1b.

The auto-calibration feature 64 may also include a sensing pin 70 located therein. The sensing pin 70 may be provided to detect when a calibration label 106 (FIG. 5) is brought into contact with the auto-calibration feature 64. The detection of the calibration label 106 may be accomplished mechanically, as through closure of a pushbutton's switch contact, or electrically, as through an electrical connection established between a sensing contact 110 (FIG. 6b) and one or more of electrical contacts 108 (FIGS. 5 and 6b). Once contact has been detected, the plurality of calibration pins 68 can determine the auto-calibration information contained on the calibration label 106. The auto-calibration feature 64 further includes one or more orienting features 72 adapted to assist a user in orienting the calibration label 106 with the plurality of calibration pins 68 within the auto-calibration feature 64. The calibration label 106 will be discussed in detail in connection with FIGS. 5-9.

Figure 2:
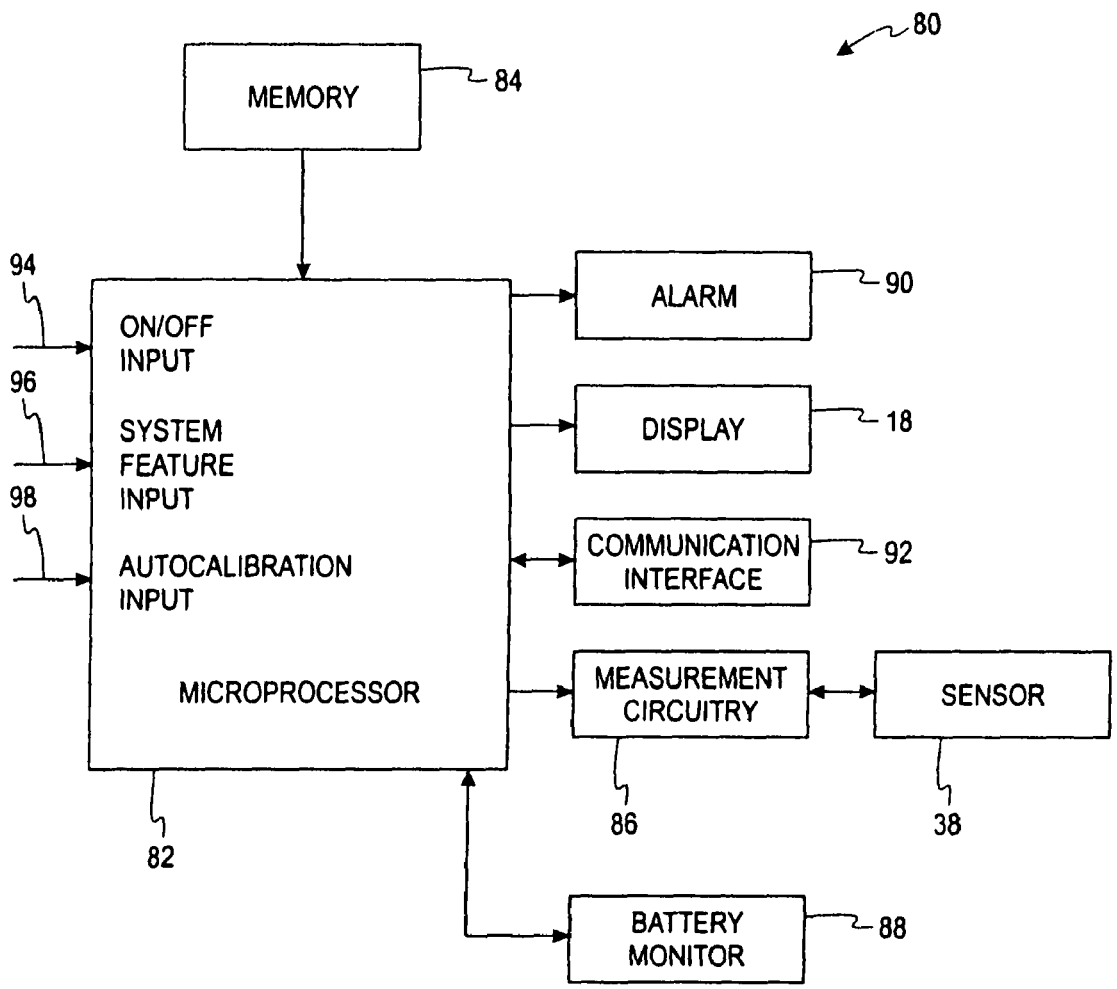
FIG. 2 is a block diagram representation of electrical circuitry of the integrated meter of FIG. 1, according to one embodiment of the invention.

As discussed above, the integrated meter 10 includes electrical circuitry 80 (FIG. 2). The electrical circuitry 80 includes various electronics and electrical components used to operate the integrated meter 10. The electrical circuitry is connected to the display 18 as well as the testing mechanism 16. Further, the electrical circuitry 80 is communicatively coupled to a memory device 84. The memory device 84 is adapted to store information such as determined analyte concentrations, whether the fluid sample was collected from an alternative test site, date and time information, lookup tables for pre-defined calibration codes, etc. The memory device 84 is typically a nonvolatile memory, such as, for example, EPROM (erasable programmable read-only memory) or EEPROM (electrically erasable programmable read-only memory). A battery (not shown) is typically used to power the electrical circuitry and display 18 within the integrated meter 10.

Referring also to FIG. 2, a block diagram representing the electrical circuitry 80 of the integrated meter 10 is illustrated, according to one embodiment of the present invention. The electrical circuitry 80 includes a microprocessor 82 together with the associated memory device 84 for storing program and user data. Sensor measurement circuitry 86 coupled to the test sensor 38 is operatively controlled by the microprocessor 82 for recording blood glucose test values. A battery monitor function 88 is coupled to the microprocessor 82 for detecting a low battery (not shown) condition. An alarm function 90 is coupled to the microprocessor 82 for detecting predefined system conditions and for generating alarm indications for the user of the integrated meter 10.

A data port or a communications interface 92 couples data to and from an external device (e.g., computer, laptop, personal digital assistant, remote server, a network-connected device, etc.). The communications interface 92 allows the external device to access at least the analyte concentrations stored in the memory device. The communication interface 92 can be any number of devices that allows the integrated meter 10 to communicate with an external device, such as, for example, a standard serial port, an infra-red emitter/detector port, a telephone jack, a radio frequency transmitter/receiver port, a modem, a removable memory card or device, etc. The electrical circuitry may also include ROM chips for carrying out programs.

An ON/OFF input 94 is responsive to the user ON/OFF operation of the integrated meter 10 and is coupled to the microprocessor 82 for performing the blood test sequence mode of the integrated meter 10. The sensor measurement circuitry 86 may also detect insertion of a test sensor 38 and cause the microprocessor 82 to perform the blood sequence mode. A system features input 96 is coupled to the microprocessor 82 for selectively performing a system features mode of the integrated meter 10. An auto-calibration input 98 is coupled to the microprocessor 82 (e.g., through interface circuitry such as that shown in FIGS. 6a and 7a) for detecting auto-calibration encoded information on a sensor container 100 (FIG. 5) in accordance with one embodiment of the present invention. The microprocessor 82 contains suitable programming to determine an analyte concentration of a fluid sample applied to the test sensor 38.

Figure 3:
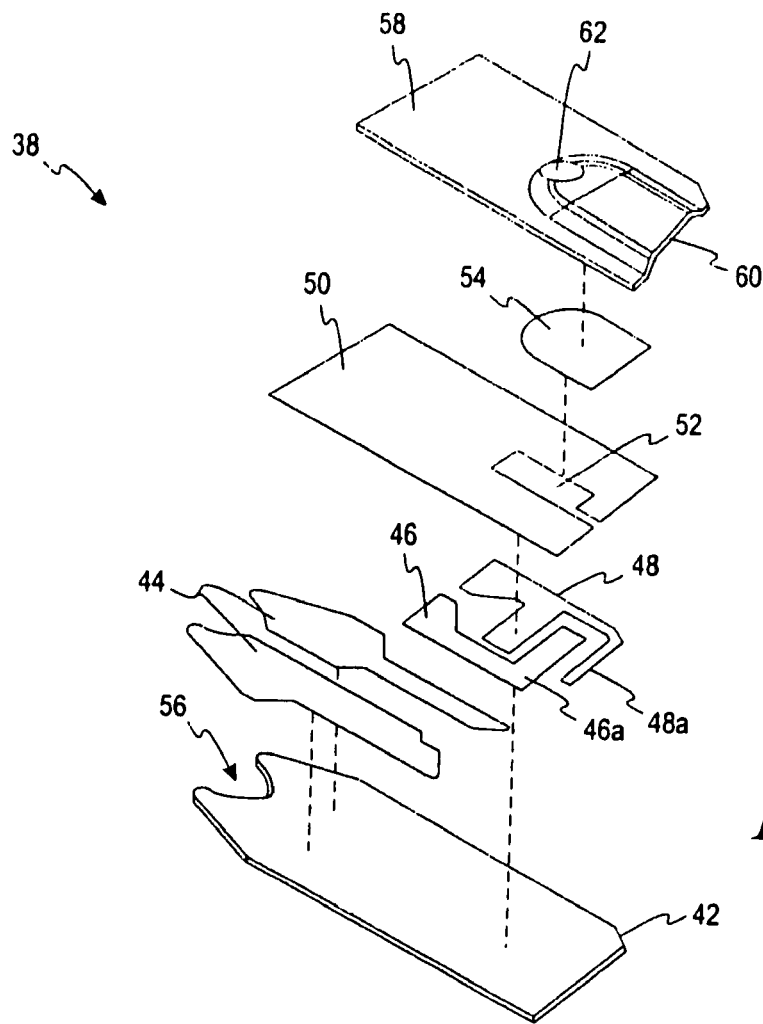
FIG. 3 is an exploded view of an electrochemical sensor according to one embodiment that may be used in a method of the present invention.
Figure 4:
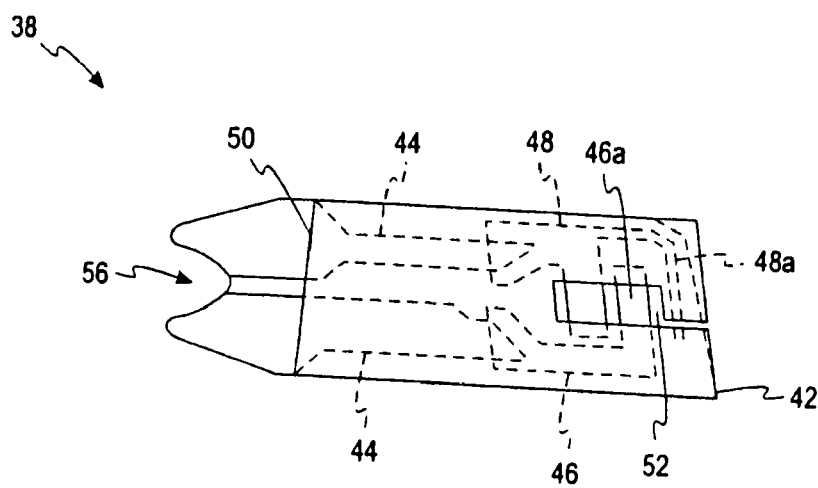
FIG. 4 is a sensor base and those elements that are applied directly to the base of the sensor in FIG. 3.

To determine the analyte concentration in a fluid sample, an electrochemical sensor can be used. It is desirable that the electrochemical sensor provides reliable and reproducible measurements. Referring now to FIG. 3, according to one embodiment, a test sensor 38 comprises an insulating base 42 upon which is printed in sequence (typically by screen printing techniques), an electrical conductor pattern 44, an electrode pattern (portions 46 and 48), an insulating (dielectric) pattern 50, and a reaction layer 54. The base of the electrochemical sensor provides a flow path for the fluid test sample. The test sensor 38 is shown in FIG. 4 in which all of the elements on the base 42 are shown in the same plane.

The function of the reaction layer 54 is to convert glucose, or another analyte in the fluid test sample, stoichiometrically into a chemical species which is electrochemically measurable, in terms of electrical current it produces, by the components of the electrode pattern. The reaction layer 54 generally contains a biosensing or reagent material, such as an enzyme, and an electron acceptor. More specifically, the reaction layer 54 contains an enzyme that reacts with the analyte to produce mobile electrons on the electrode pattern and an electron acceptor (e.g., a ferricyanide salt) to carry the mobile electrons to the surface of the working electrode. The electron acceptor may be referred to as a mediator in which the mediator is reduced in response to a reaction between the analyte and the enzyme. The enzyme in the reaction layer may be combined with a hydrophilic polymer, such as polyethylene oxide. An enzyme that may be used to react with glucose is glucose oxidase. It is contemplated that other enzymes may be used such as glucose dehydrogenase.

The two portions 46, 48 of the electrode pattern provide the respective working and counter electrodes necessary to electrochemically determine the analyte. The working electrode 46a typically comprises an enzyme that reacts with the analyte. The working and counter electrodes may be configured such that the major portion of the counter electrode 48a is located downstream (in terms of the direction of fluid flow along the flow path) from the exposed portion of a working electrode 46a. This configuration allows the test fluid sample to completely cover the exposed portion of the working electrode 46a.

A counter electrode sub-element 48a, however, may be positioned up-stream from working electrode upper element 46a so that when an adequate amount of the fluid sample (e.g., a whole blood sample) to completely cover the working electrode enters the capillary space, an electrical connection forms between counter electrode sub-element 48a and exposed portion of the working electrode 46a due to the conductivity of the fluid sample. The area of the counter electrode, however, that is available for contact by the fluid sample is so small that only a very weak current can pass between the electrodes and, thus, through the current detector. By programming the current detector to give an error signal when the received signal is below a certain pre-determined level, the sensor device may inform the user that insufficient blood has entered the sensor's cavity and that another test should be conducted.

The working and counter electrodes include electrode ink. The electrode ink typically contains electrochemically active carbon. Components of the conductor ink may be a mixture of carbon and silver that is chosen to provide a low chemical resistance path between the electrodes and the meter with which they are in operative connection via contact with the conductive pattern at a tail end 56 of the sensor. The counter electrode may be comprised of silver/silver chloride or carbon. To enhance the reproducibility of the meter reading, the dielectric pattern insulates the electrodes from the fluid test sample except in a defined area near the center of the electrode pattern 52. A defined area is important in this type of electrochemical determination because the measured current depends on the analyte concentration and the area of the reaction layer that is exposed to the analyte-containing test sample.

A typical dielectric layer 50 comprises a UV-cured acrylate modified polymethane. A lid or cover 58 is adapted to mate with the base to form a space to receive the fluid sample in which the counter and working electrodes are situated. The lid 58 provides a concave space 60, and is typically formed by embossing a flat sheet of deformable material. The lid 58 is punctured to provide an air vent 62 and joined to the insulating base 42 in a sealing operation. The lid 58 and base 42 can be sealed together by sonic welding. The embossed lid and base may be joined by using an adhesive material on the underside of the lid. The method of joining the lid and base are more fully described in U.S. Pat. No. 5,798,031 which is incorporated herein by reference in its entirety.

Suitable materials for the insulating base 42 include polycarbonate, polyethylene terephthalate, dimensionally-stable vinyl and acrylic polymers, and polymer blends such as polycarbonate/polyethylene terephthalate and metal foil structures (e.g., a nylon/aluminum/polyvinyl chloride laminate). The lid is typically fabricated from a deformable polymeric sheet material such as polycarbonate, or an embossable grade of polyethylene terephthalate, glycol modified polyethylene terephthalate or a metal foil composition (e.g., an aluminum foil structure). The dielectric layer may be fabricated from an acrylate-modified polyurethane that is curable by UV light or moisture or a vinyl polymer that is heat curable.

It is contemplated that other electrochemical sensors may be used in the present invention. Examples of electrochemical sensors that can be used to measure glucose concentrations are those used in Bayer Corporation's DEX®, DEX II®, ELITE®, and ASCENSIA® systems. More details on such electrochemical sensors may be found in U.S. Pat. Nos. 5,120,420 and 5,320,732 which are both incorporated by reference in their entirety. One or more of the electrochemical sensors may be purchased from Matsushita Electric Industrial Company. Another electrochemical sensor is disclosed in U.S. Pat. No. 5,798,031, which is incorporated by reference in its entirety. A further example of an electrochemical sensor that may be used in an amperometric monitoring system is disclosed in U.S. Pat. No 5,429,735. It is contemplated that still other biosensors may be used in the present invention.

Although the above-illustrated test sensor 38 and integrated meter 10 have been described with respect to electrochemical testing systems, it should be understood that the present invention is operable with optical testing systems or other testing systems. The electrochemical, optical, or other sensors may be stored in a sensor container such as a bottle or cartridge.

Turning now to FIG. 5, a sensor container 100 is illustrated, according to one embodiment of the present invention. The sensor container 100 includes a base 102 and a removably attachable lid 104. The base 102 is adapted to enclose a plurality of test sensors (e.g., test sensor 38) when the lid 104 is attached thereto. The sensor container 100 assists in inhibiting the contamination of the test sensors 38 by the external environment. When a test subject wishes to perform an analyte determination, one of the plurality of test sensors 38 is removed from the sensor container 100 and is inserted into the integrated meter 10 as illustrated in FIGS. 1*a-b*.

The sensor container 100 also includes the calibration label 106 located thereon. As illustrated, the calibration label 106 may be located on a portion of the lid 104. Alternatively, the calibration label 106 may be located on the base 102 or another portion of the lid 104. It should be understood that the location of the calibration label 106 on the sensor container 100 may vary so long as the calibration label 106 is able to contact the auto-calibration feature 64 (FIG. 1*b*) of the integrated meter 10. Calibration information or codes assigned for use in the clinical value computations to compensate for manufacturing variations between test sensors 38 are encoded on the calibration label 106.

The calibration label 106 is used to automate the process of transferring calibration information (e.g., the lot-specific reagent calibration information for the test sensor 38) such that the test sensors 38 may be used with different instruments or meters. One or more of the plurality of auto-calibration pins 68 electrically couples with the calibration label 106 when the calibration label 106 is brought into contact with the auto-calibration feature 64 of the integrated meter 10. According to one method, an analyte concentration of a fluid sample is determined using electrical current readings and at least one equation. In this method, equation constants are identified using the calibration information or codes from the calibration label 106. These constants may be identified by (a) using an algorithm to calculate the equation constants or (b) retrieving the equation constants from a lookup table for a particular predefined calibration code that is read from the calibration label 106. The calibration label 106 may be implemented by digital or analog techniques. In a digital implementation, the integrated meter 10 assists in determining whether there is conductance along selected locations to determine the calibration information. In an analog implementation, the integrated meter 10 assists in measuring the resistance along selected locations to determine the calibration information.

The calibration label 106 includes a plurality of electrical contacts 108 located thereon. As illustrated, the plurality of electrical contacts 108 generally surrounds an optional sensing contact 110. In embodiments where a sensing contact 110 is provided, the sensing contact 110 is adapted to engage the sensing pin 70 of the auto-calibration feature 64 to indicate to the microprocessor 82 that the auto-calibration information provided on the calibration label 106 is capable of being determined. The contact between the calibration label 106 and the auto-calibration feature 64 can be determined, for example, by sensing electrical continuity between sensing pin 70 and any of the other electrical contacts 108. In the illustrated embodiment, the calibration label 106 includes an index position 112 located between two of the plurality of electrical contacts 108. The indexing position 112 may be utilized by the auto-calibration feature 64 to determine where to begin obtaining the auto-calibration information from the calibration label 106 if more than one orientation of the calibration label 106 relative to the auto-calibration feature 64 is possible.

The sensor container 100 may also include one or more orienting features 114, as illustrated in FIG. 5. The one or more orienting features 114 of the sensor container 100 are adapted to engage the orienting features 72 (FIG. 1*b*) of the auto-calibration feature 64. As illustrated, the one or more orienting features 114 are indentations in the lid 104 of the sensor container 100. The indentations are adapted to engage the plurality of tabs that forms the orienting features 72 of the auto-calibration features. When the tabs are inserted into the indentations, the calibration label 106 of the sensor container 110 should be properly aligned with the auto-calibration feature 64 of the integrated meter 10. It should be noted, however, that alternative implementations of mechanical orienting features are possible.

Figure 6A:
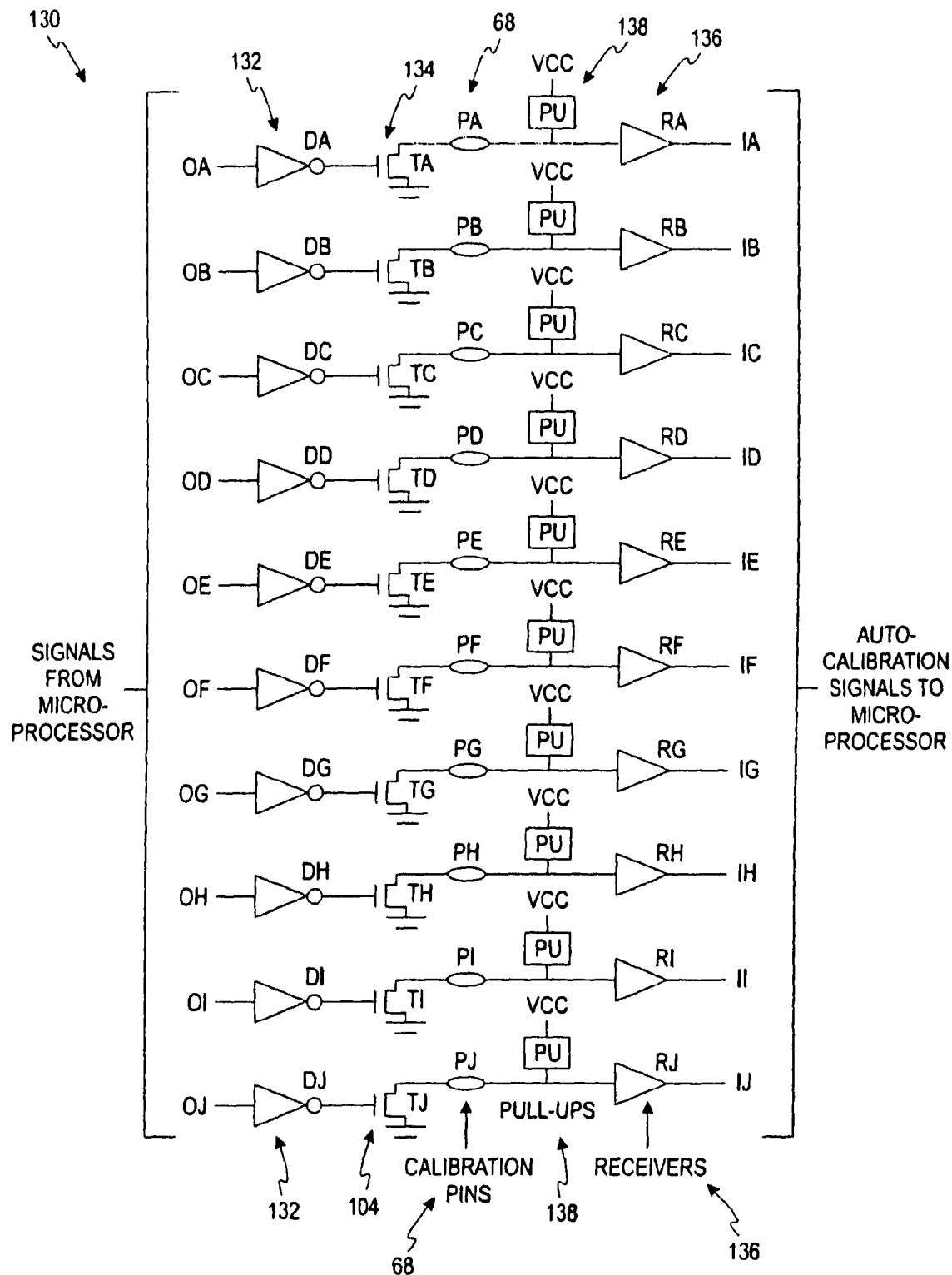
FIG. 6a is a schematic diagram representation of exemplary circuitry for use with a digital auto-calibration encoding label of the invention.
Figures 6B, 6C:
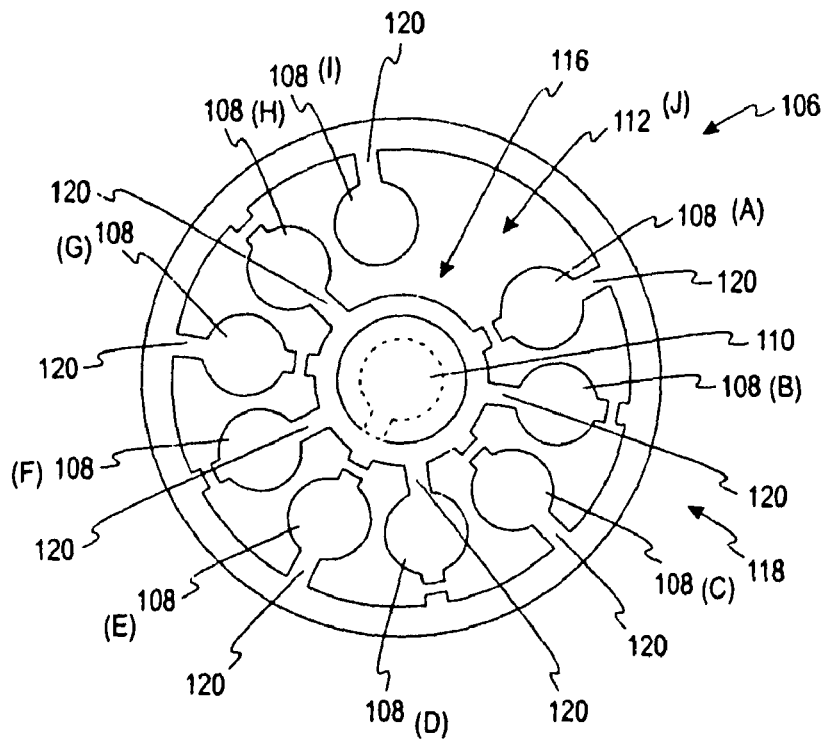
FIG. 6b is an expanded view of a digital auto-calibration encoding label, according to one embodiment of the present invention.
FIG. 6c is a chart illustrating a digital auto-calibration encoding label, in accordance with FIG. 6b.

Turning now to FIG. 6*a*, a digital electronic circuit 130 for a digital calibration method that connects the microprocessor 82 to the calibration label 106 is illustrated, according to one embodiment of the present invention. As illustrated, ten digital output signals from the microprocessor 82 (OA through OJ) connect through ten drivers 132 (DA through DJ) to the ten calibration pins 68 (PA through PJ) via the corresponding one of ten field-effect transistors (FETs) 134 (TA through TJ). The ten calibration pins 68 connect to ten receivers 136 (RA through RJ) that provide ten digital input signals (IA through IJ) to the microprocessor 82. Each receiver has an associated pull-up (PU) 138 connected to a supply voltage (VCC). The calibration pins 68 (PA through PJ) electrically connect to other electrical contacts 108 on the calibration label 106.

To read a contact pattern of the calibration label 106, the microprocessor 82 turns on one of the drivers 132, all other drivers 132 are turned off. The enabled driver 132 presents a low signal to the associated calibration pin 68. The corresponding receiver 136 for the enabled driver 132 directly connected to the associated calibration pin 68 reads as a low signal since this particular driver 132 and receiver 136 are directly connected. All other receivers 136 whose calibration pin 68 is also driven low by the label pattern are also read as a low signal. All remaining other receivers 136 read as a high signal since the associated driver 132 is not turned-on and the associated pull-up 138 pulls the receiver voltage to VCC.

Referring now to FIG. 6*b*, there is shown an enlarged view illustrating a preferred arrangement of the calibration encoded calibration label 106 of the invention. According to one embodiment, the calibration-encoded calibration label 106 is used to automate the process of information transfer about the lot-specific reagent calibration assigned to the associated test sensors 38. For example, the auto-calibration information as illustrated in FIG. 6*b* can be encoded into the calibration label 106 that is located on the sensor container 100 enclosing a plurality of test sensors 38 having a common origin or lot. The calibration label 106 is read at any angular position and deciphered by the integrated meter 10 without any user intervention. The calibration label 106 is read via the plurality of electrical contacts 108 provided at predetermined positions. The selected ones of the electrical contacts 108 are connected to an inner ring 116 by a conductive trace 120. Other electrical contacts 108 are connected to an outer ring 118 by a conductive trace 120 while still other electrical contact(s) 108 not connected to either the inner ring 116 or the outer ring 118. The non-connected contact(s) may be used to establish the orientation of the label relative to the auto-calibration feature 64 while the electrical contacts 108 connected to the inner ring 116 and the outer ring 118 may be used to encode calibration data.

Figure 7A:
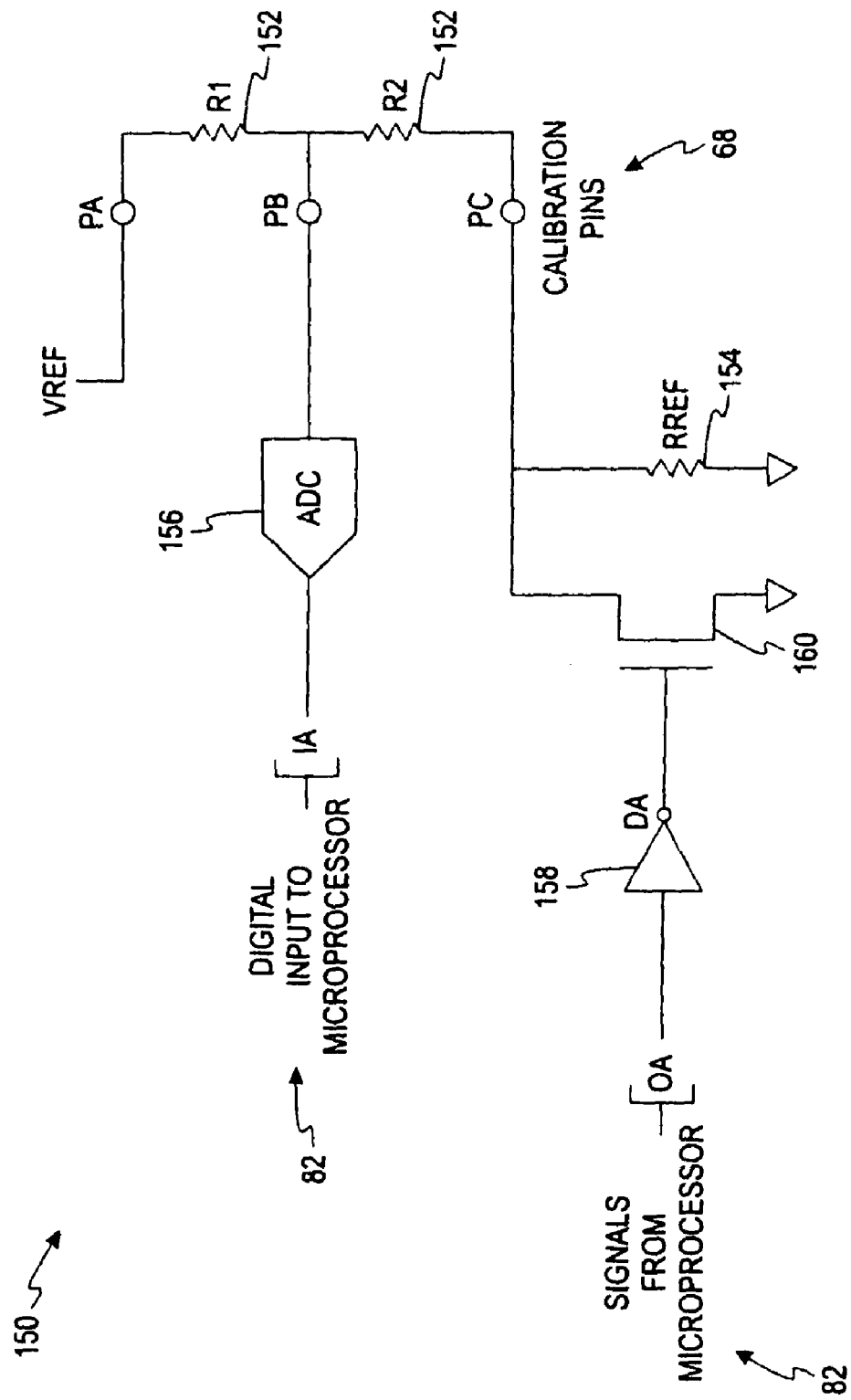
FIG. 7a is a schematic diagram representation of exemplary circuitry for use with an analog auto-calibration encoding label, according to another embodiment of the present invention.
Figure 8A:
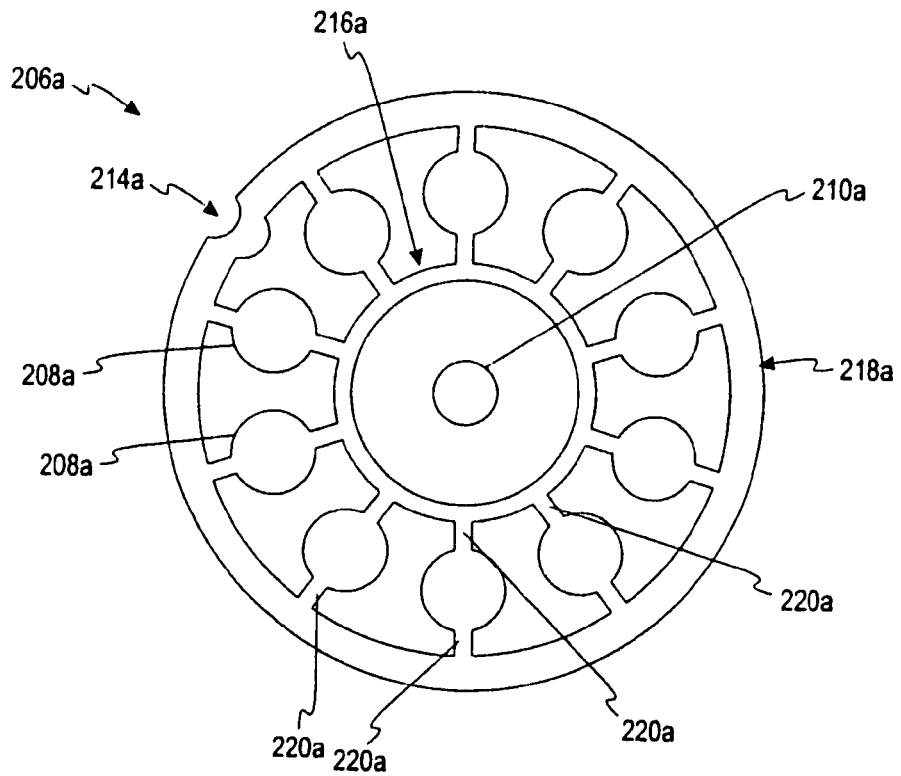
FIGS. 8a-e are top views of a plurality of calibration labels with locating features, according to some embodiments of the present invention.
Figure 8B:
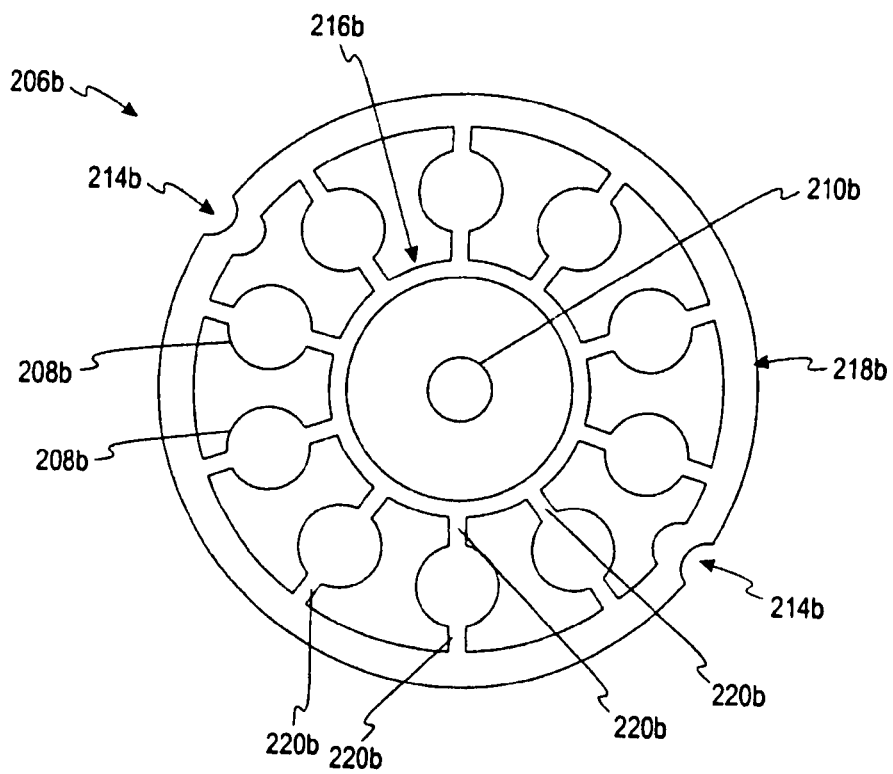
Figure 8C:
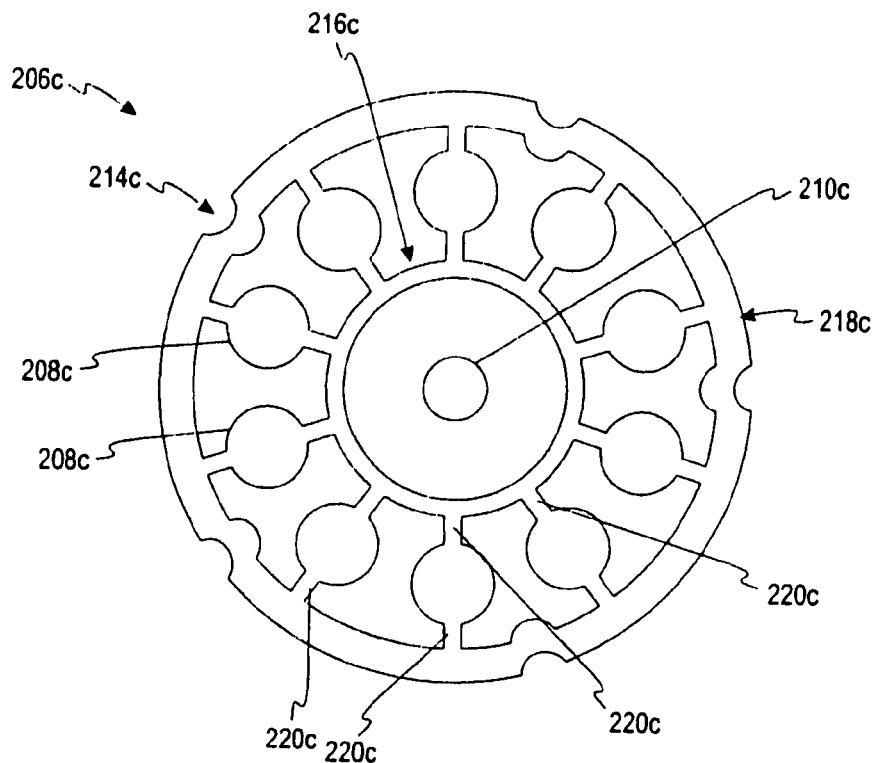
Figure 8D:
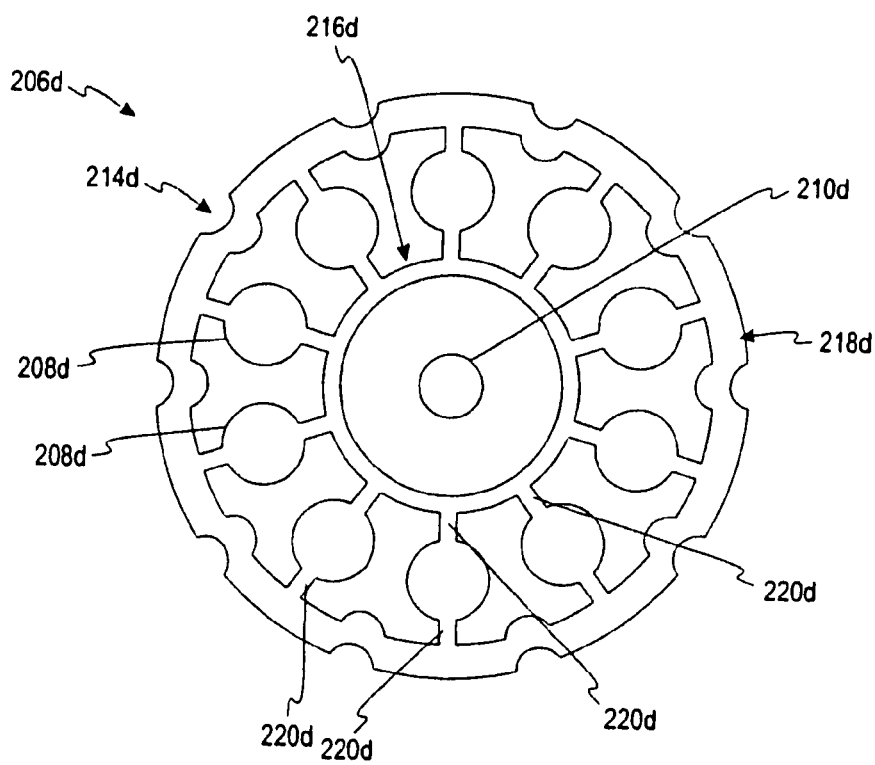
Figure 8E:
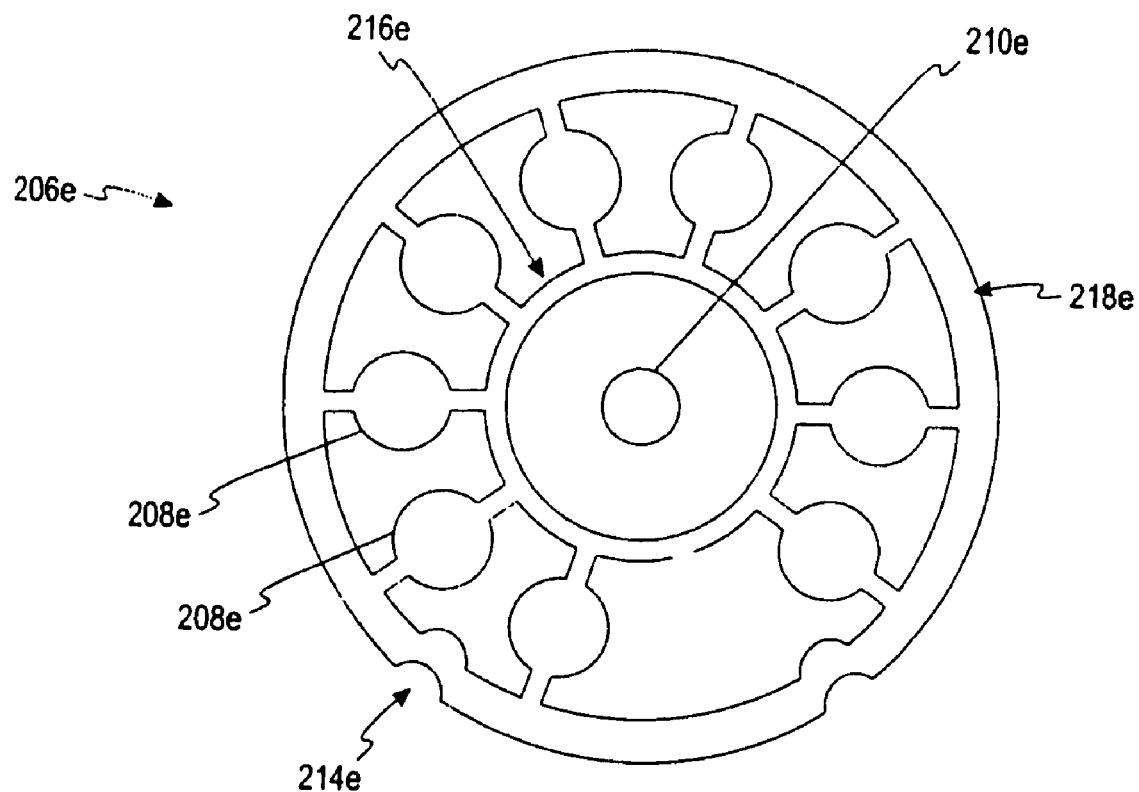

A number of both digital and analog arrangements can be employed to define the calibration label 106. The calibration label 106 can be constructed by screenprinting conductive ink onto a base substrate that can either be a separate substrate or the sensor container 100 (FIG. 5). A separate substrate can be attached to the sensor container 100 using an adhesive (e.g., a hot melt, UV-cure, or fast-curing adhesive) or via other attachment means. A conductive ink defining the calibration label 106 may be a carbon, silver, or a carbon/silver blended ink. The substrate may be any print receptive surface including paper, polymer-filled paper, or polymer substrate, and in some embodiments is a heat stabilized polyethyleneteraphthalate (PET) or polycarbonate. Digital calibration encoding can be defined by either direct encoding through printing or cutting traces with a laser, such as a $CO_2$ or Nd:YAG laser, for a particular test sensor lot. In alternative embodiments, a metal film, such as a thin aluminum film, may be utilized to form the traces and may be ablated by a laser to form a calibration pattern to encode the calibration data. An analog system as illustrated and described with respect to FIGS. 7a-d may be used that is based on measuring resistors that are selectively located at predefined positions, for example, represented by lines 152 and connected to the selected contacts O, I, J as shown in FIG. 7b.

FIG. 6b illustrates an exemplary trace pattern for the calibration label 106. As shown in FIG. 6b, the calibration label 106 includes three sets of contact connections: first electrical contacts 108, A, C, E, G, and I connected to the outer ring or path 118 representing a logical 1; second electrical contacts 108, B, D, F, and H connected to the inner ring or path 116 representing a logical 0; and third null contact or no connection (e.g., index position 112) representing the home position or sync. It should be understood that the inner and outer rings 116, 118 do not have to be complete rings or circles. The electrical contacts 108 and the conductive traces 120 that form the inner and outer rings 116, 118 are made of an electrically conductive material. The position of the electrical contacts 108 are aligned with calibration pins 68 (shown in FIG. 1b) incorporated into the auto-calibration feature 64 of the integrated meter 10 to make electrical contact. While in some embodiments the calibration label 106 may be positioned in any one of multiple rotary positions, the electrical contacts 108 will always be in alignment with the calibration pins 68 on the integrated meter 10 when the calibration label 106 is read. The table of FIG. 6c applies to the calibration label 106 of FIG. 6b.

The index position 112 may include one sync contacts similar to the electrical contacts 108. The sync electrical contact 108 is not illustrated on the calibration label 106, since it is not connected to any other of the plurality of electrical contacts 108. Alternate implementations are possible with more than one sync contact. Specific contact(s) 108 may optionally be designated for connection always to the inner ring 116 or outer ring 118. In FIG. 6B, the contact labeled I is illustrated as always being connected to the outer ring 118. The electrical contacts 108 labeled A through H connect to both rings in an unprogrammed label. A cut is made in the printed conductive label material to disconnect the contact from the inner or outer ring 116, 118 to program the calibration code into the calibration label 106. Each one of the electrical contacts 108 A through H could be connected to either ring, this represents $2^8$ (i.e., two hundred fifty-six) possible combinations. Code 0 (A through H all connected to inner ring), codes 127, 191, 223, 239, 247, 251, 253, and 254 (only one of A through H connected to the inner ring), and code 255 (A through H all connected to outer ring) are typically not permitted, so two hundred forty-six codes can be programmed with calibration encoded calibration label 106.

To determine which electrical contacts 108 are the sync contacts (e.g., index position 112), and which electrical contacts 108 are connected to the inner and outer rings 116, 118, one electrical contact 108 at a time is set as a low output (zero). Any electrical contacts 108 that are on the same ring 116, 118 as the low contact will also register low due to the electrical connection provided by the conductive traces on the calibration label 106. Because the sync contact(s) are not connected to either ring 116, 118, they register as the only low contact when set low. This means that there must be at least two contacts connected to both the inner and outer rings 116, 118, otherwise, it would be impossible to determine which contacts are the sync contact(s).

A method for determining the auto-calibration number can use two more readings than the number of sync contacts of the calibration label 106. Each of the readings is for one set of the electrical contacts 108: the set connected to the inner ring 116, the set connected to the outer ring 118, and one for each sync contact. After this minimal number of readings are taken, it is possible to determine the electrical contacts 108 that correspond to each of the four sets. Where only a single sync position is utilized, the decoding can be accomplished with as few as three readings. If there are two sync contacts, four readings are required. The position of the sync contacts are determined and this is used in conjunction with the reading from the set connected to the inner ring 116 to determine the auto-calibration number. The electrical contacts 108 connected to the inner ring 116 are considered logical zeroes, and the electrical contacts 108 connected to the outer ring 116 are considered logical ones.

A selected predefined calibration encoded pattern consists of the electrical contacts 108 interconnected by the conductive inner and outer rings 116 and 118. Calibration data is encoded using selectively electrically interconnected sets of contacts on the calibration label 106. One or more null contact positions 112 are isolated from both rings 116 and 118 to serve as a rotary position index. One of the electrical contacts 108 at some known position relative to the sync position (represented by contact I) connects to the outer ring 118 so all connections to this contact TO are logical ones. 100781 To detect a connection to the inner ring 116 or outer ring 118, at least two connections to that ring are needed to detect continuity. The remaining electrical contacts 108 are connected to one or the other rings 116 and 118, the particular connection pattern identifying the calibration code. To minimize label stock, a single pattern advantageously is used with subsequent punching or cutting to isolate selectively each of eight pads, positions A through H, from one of the two rings 116 or 118. All electrical contacts 108, positions A through H, except the index or null position(s), are connected to one, and only one, of the two rings 116, 118. A minimum of two electrical contacts 108 are connected to each ring 116, 118. This arrangement facilitates error checking since all of the electrical contacts 108—except for the index position 112—must be accounted for in one of two continuity groups for a reading to be considered valid. A missing calibration label 106 is detected when all contacts appear to be a sync contact (i.e., there are no electrical connections between calibration pins 68 because the continuity provided by the calibration label 106 is missing).

In one digital encoding method a series of open and closed circuits representing 0 and 1 are introduced onto the calibration label 106. A digital calibration label 106 is encoded by laser cutting or printing to represent a particular calibration code number determined by the connections to the inner ring 116, for example, where A represents 1, B represents 2, C represents 4, D represent 8, E represents 16, F represents 32, G represents 64, and H represents 128. In FIG. 6c, contacts B, D, F, and H are connected to the inner ring 116 to define the calibration code number.

The microprocessor 82 configures one electrical contact 108 or bit as a low while the other remaining electrical contacts 108 are high. All electrical contacts 108 electrically connected to the particular driven electrical contact 108 are forced low while the remaining electrical contacts 108 are pulled high. By selectively driving the electrical contacts 108 and reading the resulting input patterns, the interconnection pattern and associated calibration code is determined. While the unique index position 112—defined by no connection to another contact—is used to determine the rotary position of the calibration label 106 so that the electrical contacts 108, A through I can be identified, it should be understood that other configurations can be used with unique patterns of bits to both encode starting position and the calibration code. However, other binary coding schemes may provide fewer possible codes for the calibration code number with the same number of electrical contacts 108.

Figure 6D:
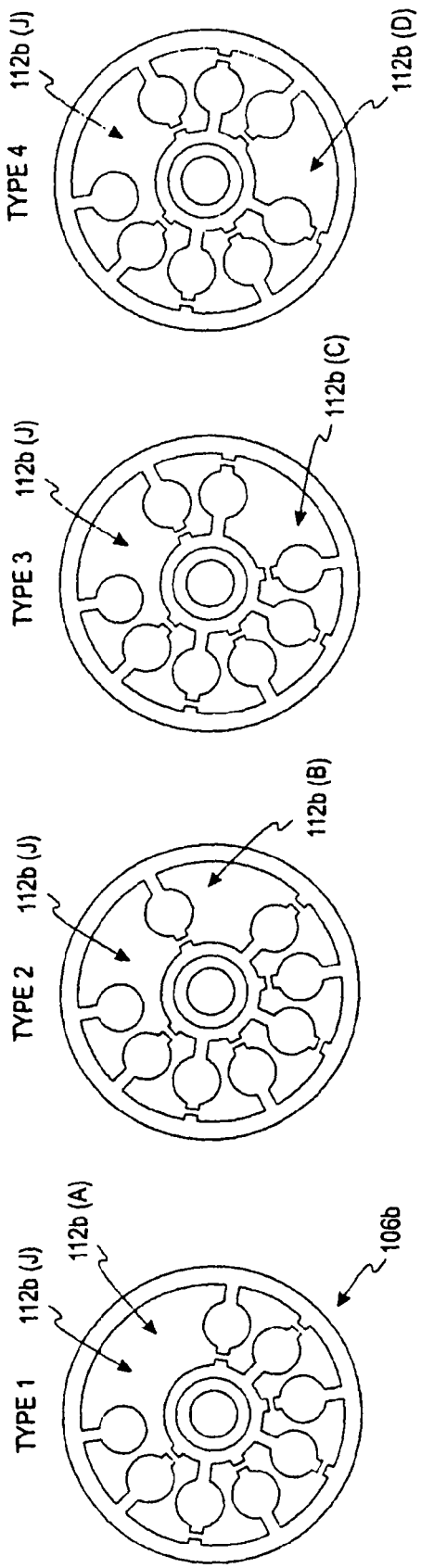
FIG. 6d is an expanded view of a plurality of digital auto-calibration encoding labels, according to another embodiment of the present invention.

Alternative calibration encoded labels 106b for encoding of the calibration information are illustrated in FIGS. 6d and 6e, respectively. In any calibration label 106 and 106b, the actual physical locations of the contacts relative to each other is not important for decoding the calibration label 106 as long as they are in known or predefined positions.

Referring to FIGS. 6d and 6e, ten electrical contacts 108 are represented by contact A through contact J. As in FIG. 6d, there are three groupings or sets of contact connections including two index positions 112b (SYNC), outer ring 118 (OUTER), and inner ring 116 (INNER). In FIG. 6d for the calibration encoded calibration label 106b with ten contacts A through J, contact J is SYNC 1, contact A is SYNC 2, and one must be tied to the outer ring shown as contact I, and the remaining eight contacts B through H are connected to either the inner ring 116 or the outer ring 118. The eight contacts B through J (codes 0 through 255) represent 256 ($2^8$) possible combinations of connections, minus eight combinations for only one inner ring connection (codes 127, 191, 223, 239, 247, 251, 253, 254), minus one combination for only one outer ring connection (code 0). The calibration label 106b provides 247 unique combinations or codes for the calibration number.

The calibration codes on a particular calibration label 106 can also be used to distinguish between several types of test sensors 38. Suppose sensor type "A" required ten calibration codes, sensor type "B" required twenty calibration codes, and sensor type "C" required thirty calibration codes. The auto-calibration codes could be assigned so codes one through ten signify a type "A" sensor with type "A" calibration code one through ten, label codes eleven through thirty signify a type "B" sensor with type "B" calibration code one through twenty, and label codes thirty-one through sixty signify a type "C" sensor with type "C" calibration code one through thirty. In this example, the label code indicates both the sensor type and calibration code associated with that sensor type.

In FIG. 6d, alternative types 1, 2, 3, and 4 of the calibration labels 106b include two sync positions 112b. In the type 1 calibration label 106b two adjacent sync positions are used. With the type 1 calibration label 106b, the two adjacent sync contacts are J and A, one contact I is tied to the outer ring 118, and the seven remaining contacts B through H are connected to the inner or outer ring 116, 118. The seven contacts represent 128 ($2^7$) possible combinations of connections, minus seven combinations for only one inner ring connection, minus one combination for only one outer ring connection. The type 1 calibration encoded calibration label 106b provides 120 unique combinations for the calibration number.

With the type 2, 3, and 4 calibration labels 106b, the relative position of the two sync contacts can be used to provide additional information. Sync contact combinations J and A (no gap) type 1, J and B (gap of one space) type 2, J and C (gap of two spaces) type 3, and J and D (gap of three spaces) type 4 can be uniquely detected and used to distinguish between four types of calibration labels 106b, each calibration encoded calibration label 106b encoding 120 unique combinations. Sync contact combinations J and E, J and F, J and G, J and H, and J and I are not uniquely distinguishable. Using the four types 1, 2, 3, and 4 of calibration labels 106b provides a total of 480 (**4\* 120**) combinations for the calibration number.

Other calibration labels 106 can be provided with the relative position of three or more sync contacts used to generate unique patterns. For example, with three sync contacts and one contact tied to the outer ring 118, six contacts remain to connect to the outer or inner ring 116, 118. The six contacts represent sixty-four ($2^6$) possible combinations of connections, minus seven combinations for only one inner ring connection, minus one combination for only one outer ring connection which leaves fifty-six unique combinations. There are many ways that the three sync contacts can be uniquely placed: J, A, and B; J, A, and C; J, A, and D; J, A, and E; J, A, and F; J, A, and G; J, A, and H; J, B and D; J, B, and E; etc. As with two sync contacts, these combinations of sync contacts can indicate different types of labels, and for example, to identify one of multiple types of analysis to be performed by the integrated meter 10.

Figures 6F, 6G:
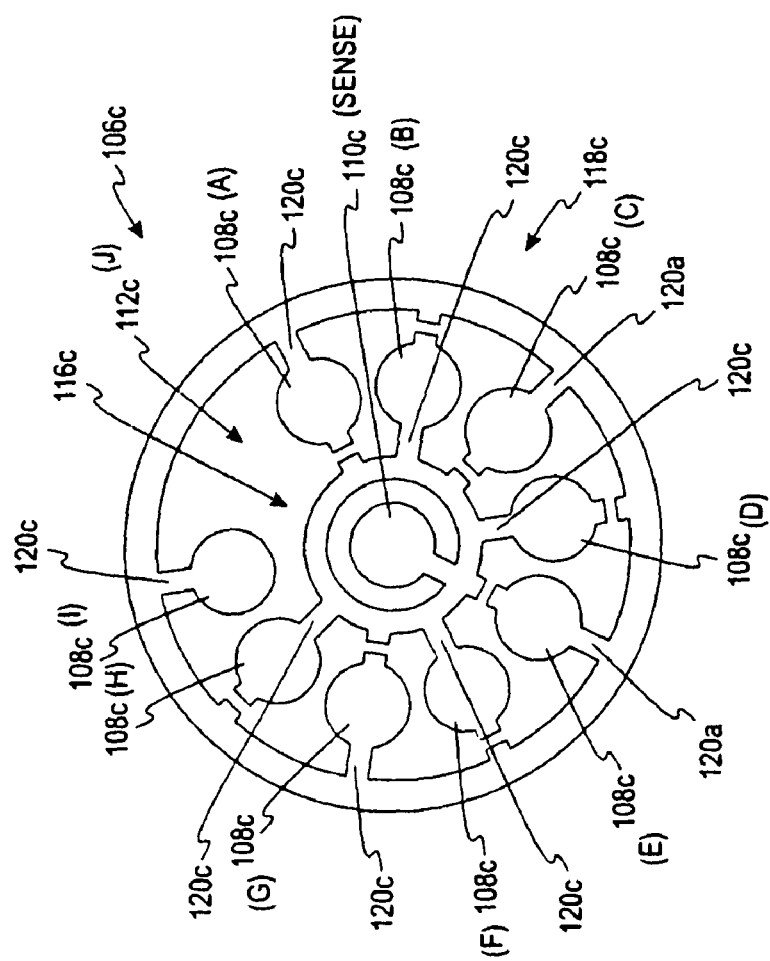
FIG. 6f is an expanded view of a plurality of digital auto-calibration encoding labels, according to another embodiment of the present invention.
FIG. 6g is a chart illustrating a digital auto-calibration encoding label, in accordance with FIG. 6f.

Referring also to FIGS. 6f-g, a digital auto-calibration encoding label 106c is illustrated, according to one embodiment of the present invention. The calibration label 106c utilizes only a single index location 112c to maximize the information capable of being encoded onto the electrical contacts 108c. In some embodiments, more index positions may be utilized. In the illustrated embodiment, the sensing contact 110c is connected to at least one of the inner ring 116c or the outer ring 118c by an electrical trace 120c. If the sensing contact 110c is forced low, at least one electrical contact 108c is pulled low. In this implementation, at least one electrical contact 108c that is pulled low may be used as an indication that the calibration label 106c is in contact with the auto-calibration feature 64 (FIG. 1b). According to one embodiment, the sensing contact 110c is located in a position that is independent of the calibration label's 106c orientation relative to the auto-calibration feature 64.

In FIG. 7a, an analog electronic circuit 150 is illustrated, according to one embodiment. The analog electronic circuit 150 is based on measuring resistance values of resistors 152 (R1 and R2) provided on a calibration label 106d (as best illustrated in FIG. 7b), or a calibration label 106e (as best illustrated in FIG. 7C). The resistance value of resistors 152 (R1 and R2) provides the calibration value. Continuity between the central contact and any other electrical contact 108 can be used as an indication that the calibration label 106e is in contact with the auto-calibration feature 64 of the instrument. Although it is possible to relate the analog value of the resistance to the calibration value, the typical arrangement is to print resistors 152 of specific values. For example, to distinguish five calibration codes one of five different resistance values (e.g. 1000Ω, 2000Ω, 3000Ω, 4000Ω, and 5000Ω) would be screen printed onto the calibration label 106d, 106e. The resistance values for resistors 152 (R1 and R2) are chosen so the resistance values measured by the microprocessor 82 are easily distinguished from each other even though there may be variations in the resistance due to printing variations or variations in contact resistance where the calibration label 106*d*, 106*e* is contacted by the calibration pins 68.

In FIG. 7*a*, a known reference voltage (VREF) and resistor 154 having a known reference resistance (RREF) are illustrated. An analog-to-digital converter (ADC) 156 converts the analog voltage present at its input labeled VMEAS into a digital value at its output labeled (IA) which is read by the microprocessor 82. A driver 158 (DA) is an analog switch controlled by the microprocessor 82 through a signal line labeled OA. The driver 158 controls a p-channel field-effect transistor (FET) 160 that leaves the resistor 154 RREF in the analog electronic circuit 150 when the driver 158 is turned off or shorts out the resistor 154 RREF when the driver 158 is turned on.

The value of the resistors 152 (R1 and R2) can be determined as follows. With the driver 158 DA turned off, the resistor 154 RREF is in the circuit, so the resistors 152 (R1 and R2) plus the resistor 154 RREF function as a voltage divider. Then the voltage VMEAS is measured and defined as VOFF. With the driver 158 DA turned on, RREF is shorted out, so the resistors 152 (R1 and R2) function as a voltage divider. Then the voltage VMEAS is again measured and now defined as VON.

The applicable equations are:

$$VOFF = \frac{R2 + RREF}{R1 + R2 + RREF} VREF \quad [\text{equ 1}]$$

$$VON = \frac{R2}{R1 + R2} VREF \quad [\text{eqn 2}]$$

solving eqn 2 for R1:

$$R1 = R2 \frac{VREF - VON}{VON} \quad [\text{equ 3}]$$

substituting R1 into eqn 1 and solving for R2:

$$R2 = RREF \frac{VON(VREF - VOFF)}{VREF(VOFF - VON)} \quad [\text{eqn 4}]$$

REF and RREF are known values and VOFF and VON are measured values. In eqn 3, the values for R2, VREF, and VON are substituted to calculate R1. At this point R1 and R2 are known so the calibration value can be determined.

To distinguish many calibration codes, more than one resistor could be used. For a calibration label 106*d*, 106*e* with "m" resistors where each resistor may be any of "n" values, then the number of calibration codes is $m^n$.

For example, printing two resistors 152 (R1 and R2)—where each resistor 152 could have one of five distinct resistance values—permits twenty-five (i.e., $5^2$) calibration codes to be distinguished. This can be expanded to three resistors 152 and could provide 125 (i.e., $5^3$) calibration codes, and so on.

Having reference to FIG. 7*b*, a two-resistor 152 analog calibration label 106*d* is illustrated, according to one embodiment. An inner resistor 152 (R2) and outer resistor 152 (R1) can be replicated ten times (once for each rotary position of the calibration label 106*d*) while only three calibration pins 68 are needed, as shown in FIG. 7*a*. The calibration pins 68 are placed in a line. One calibration pin 68 (PA) would contact the electrical contact 108 at the common junction (I) of all the inner resistors 152 (R2). Another calibration pin 68 (PB) contacts the electrical contact 108 at a junction (J) of the inner resistor R2 and the outer resistor 152 R1. The third calibration pin 68 (PC) contacts the electrical contact 108 at the other end (O) of the outer resistor 152 (R1).

A variation of the calibration label 106*d* of FIG. 7*b* can have only one inner resistor 152 (R2) and one outer resistor 152 (R1), with continuous conductive rings to make contact with the calibration pins 68. One ring (not shown) would be at the diameter of the junction (J) of resistors 152 (R1 and R2). The other ring (not shown) would be located at the diameter of the other end (O) of resistor 152 R1. The conductive rings would be made of low resistance material. The calibration pins 68 would contact the center contact (I) and the two rings, as with the label 106*d*.

Another style of a two-resistor calibration label 106*b* is illustrated in FIG. 7*c*. The three calibration pins 68 are again placed in a line. One calibration pin 68 (PB) would contact the electrical contact 108 at a junction 178 of all ten resistors 152. Another calibration pin 68 (PA) would connect to the end 174 of resistor R1. The third calibration pin 68 (PC) would be in a line with the other two calibration pins 68 and connect to the electrical contact 108 at the end 176 of the resistor R2. If the set of resistance values for resistance R1 (e.g., n1 values) were different than the set of resistance values for resistance R2 (e.g., n2 values) then n1*n2 different calibration codes could be distinguished.

For the calibration label 106*e*—illustrated in FIG. 7*c*—where the values of the two resistors 152 are chosen from the same set of "n" resistances then some combinations are not distinguishable because the label rotates (e.g., R1=1000Ω and R2=2000Ω cannot be distinguished from R1=2000Ω and R2=1000Ω). The number of different combinations of two resistors of the style of the calibration label 106*e*, where each resistor may be one of "n" values is given by the equation:

$$\text{Combinations} = \frac{n(n-1)}{n} + n \quad [\text{equ 5}]$$

Referring also to FIG. 7*d*, the number of different resistance values and the number of distinct calibration codes that can be determined is tabulated.

Turning now to FIGS. 8*a-e*, a plurality of calibration labels 206*a-e* respectively is illustrated, according to some embodiments of the present invention. Each of the calibration labels 206*a-e* include a plurality of electrical contacts 208*a-e* located around an optional sensing contact 210*a-e*. Each of the electrical contacts 208*a-e* is initially connected to both an inner ring 216*a-e* and an outer ring 218*a-e* by a plurality of conductive traces 220*a-e*. The calibration information is encoded onto the calibration label 206*a-e* by removing a portion of the conductive traces 220*a-e* to disconnect one or more of the electrical contacts 208*a-e* from the inner ring 216*a-e*, the outer ring 218*a-e*, or both. A sync position is encoded by removing the conductive traces 220*a-e* to disconnect an electrical contact(s) 208*a-e* from both the inner rings 216*a-e* and the outer rings 218*a-e*.

Each of the calibration labels 206*a-e* is provided with at least one label-orienting feature 214*a-e*. The number of label-orienting features 214*a-e* varies, by way of example, for each of the calibration labels 206*a-e*. If the label-orienting features 214*a-d* are symmetrically positioned around the periphery of the calibration labels 206*a-d*, as illustrated in FIGS. 8*a-d*, the calibration labels 206*a-d* may be rotated into a variety of positions before being applied to the auto-calibration feature 64 (FIG. 1*b*) of the integrated meter 10. The orientation of these calibration labels 206*a-d* relative to the auto-calibration feature 64 may be established by selectively isolating one or more sync contacts from both label rings. Alternatively, in FIG. 8*e*, the calibration label 206*e* includes a plurality of label-orienting features 214*e* that is asymmetrically positioned around the calibration label 206*e*. As such, the label-orienting features 214*e*—in combination with a plurality of asymmetrical orienting features 72 on the auto-calibration feature 64—assist with ensuring that the calibration label 206*e* is only applied to the plurality of calibration pins 68 of the auto-calibration feature 64 in a specific orientation.

Figure 9A:
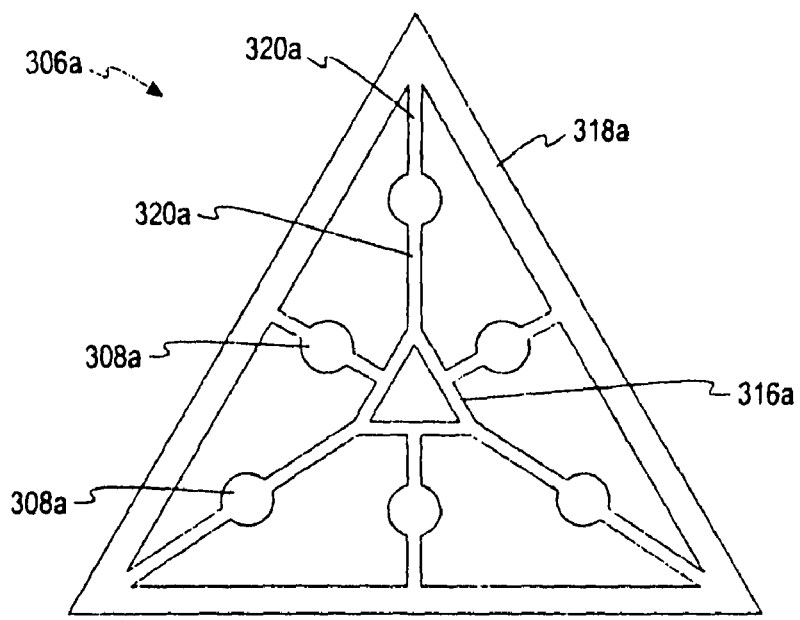
FIGS. 9a-9f are top views of a plurality of calibration labels with locating features, according to some other embodiments of the present invention.
Figure 9B:
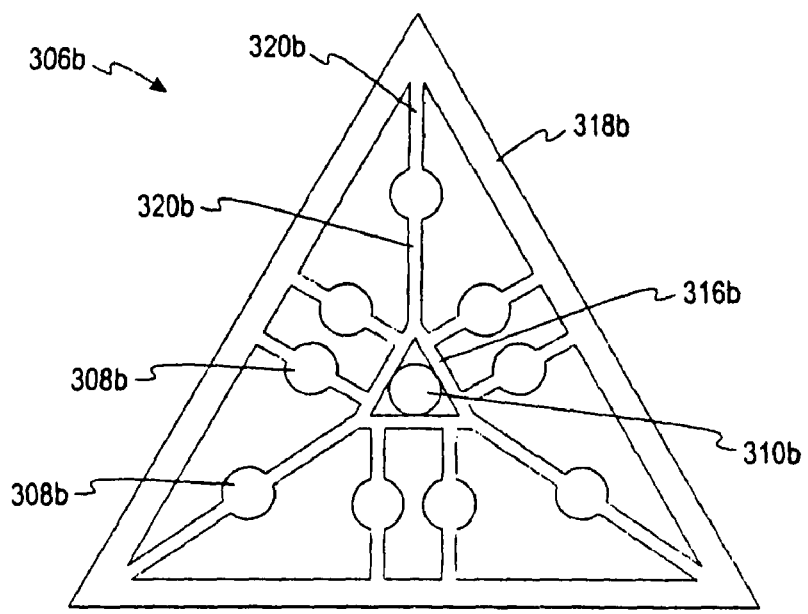
Figure 9C:
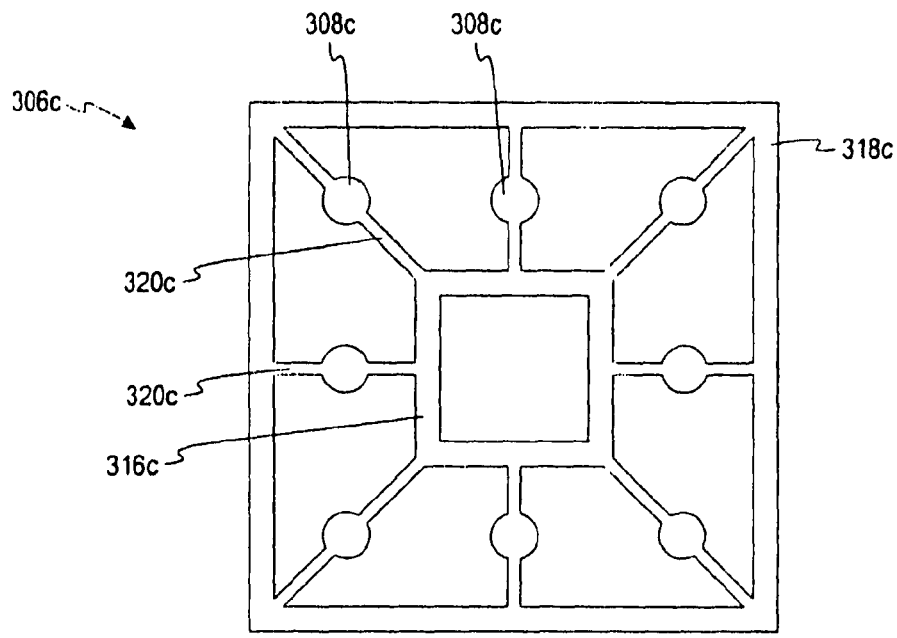
Figure 9D:
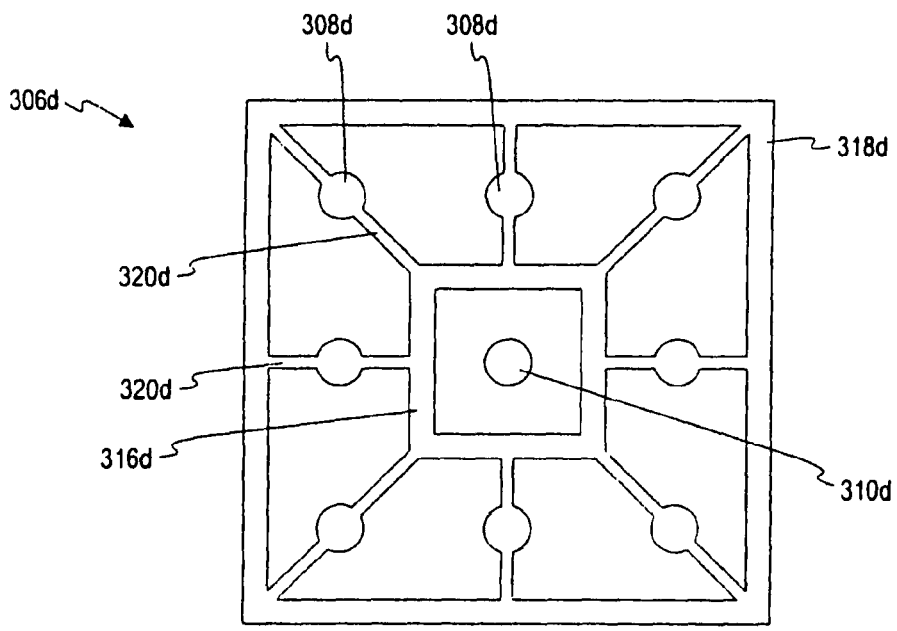
Figure 9E:
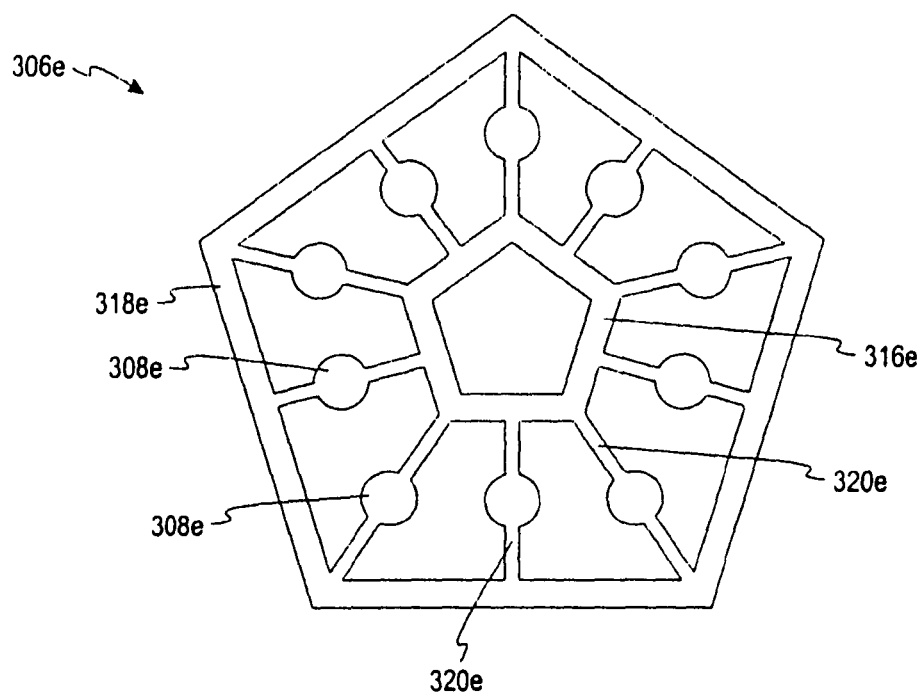
Figure 9F:
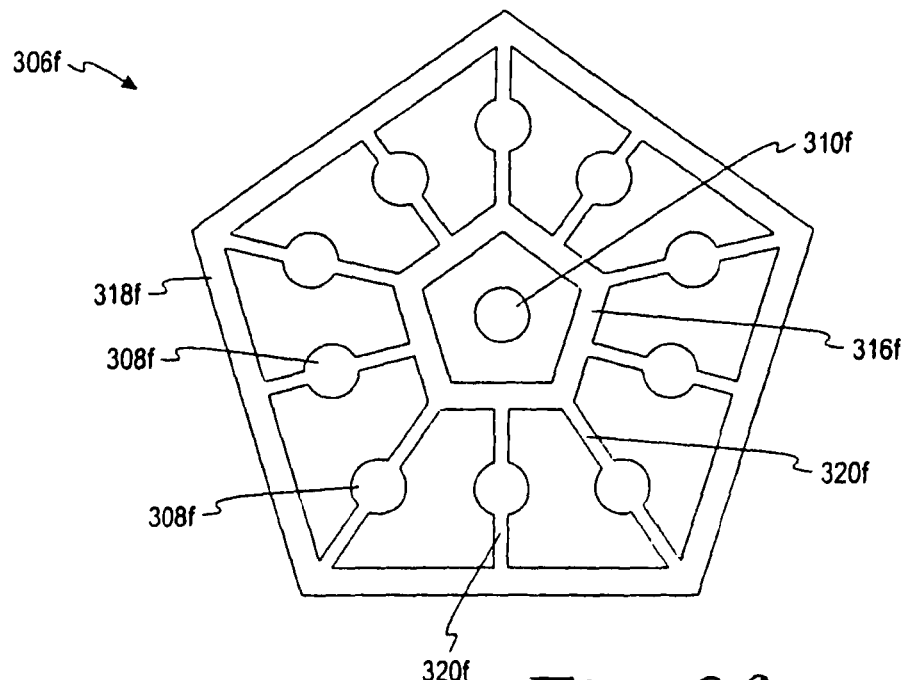

Referring now to FIGS. 9*a*-9*f*, a plurality of calibration labels 306*a-f* is illustrated, according to various embodiments of the present invention. Each of the calibration labels 306*a-f* include a plurality of electrical contacts 308*a-f*. In FIGS. 9*b*, 9*d*, and 9*f*, the plurality of electrical contacts 308*b*, 308*d*, 308*f* is generally located around an optional sensing contact 310*b*, 310*d*, 310*f*. Each of the electrical contacts 308*a-f* is initially connected to both an inner ring 316*a-f* and an outer ring 318*a-f* by a plurality of conductive traces 320*a-f*. The calibration information is encoded onto the calibration label 306*a-f* by removing a portion of the conductive traces 320*a-f* to disconnect one or more of the electrical contacts 308*a-f* from the inner ring 316*a-f*, the outer ring 318*a-f*, or both. The orientation of these calibration labels 306*a-f* relative to the auto-calibration feature 64 may be established by selectively isolating one or more sync contacts from both label rings.

The above-described embodiments of the calibration labels have been illustrated as being generally symmetrical around the periphery of the calibration labels. In alternative embodiments, the calibration labels are asymmetrical allowing for only one orientation of the calibration label with the auto-calibration feature of an integrated meter. In these embodiments, the calibration labels may further include label-orienting features to assist a user in properly aligning the calibration labels. Alternatively, the asymmetric shape of the calibration label may facilitate the proper alignment of the calibration label.

Figure 10:
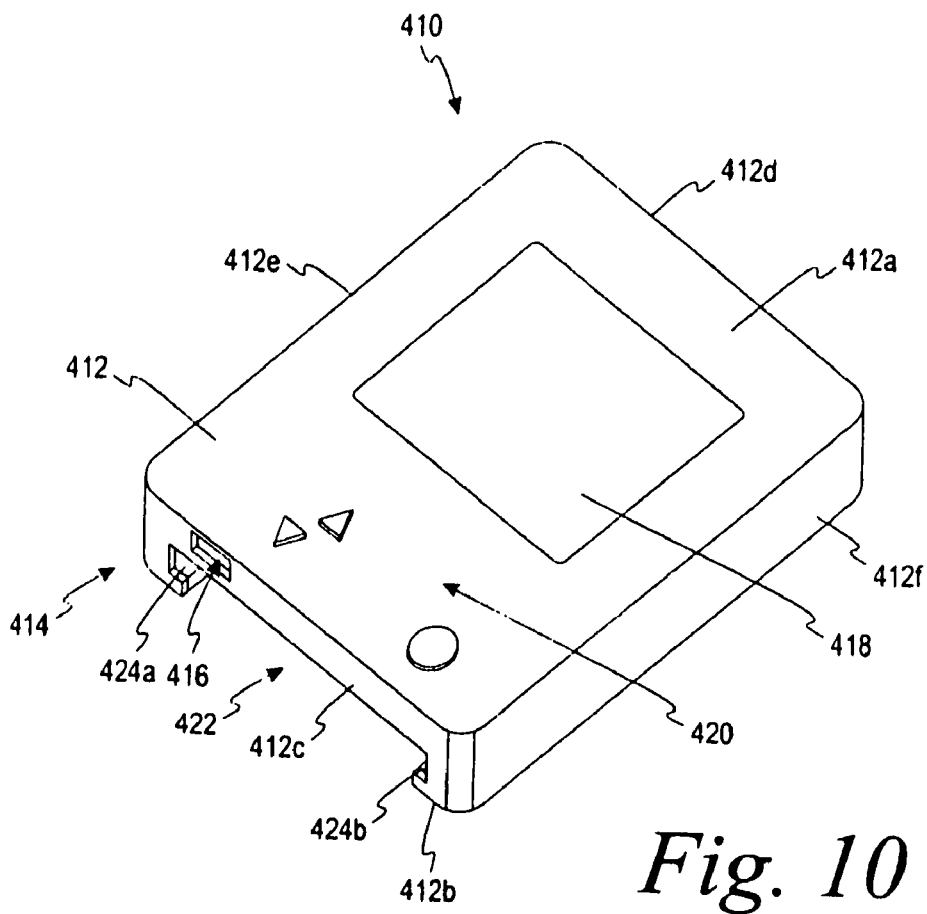
FIG. 10 is a perspective view of a meter adapted to seat a sensor container, according to one embodiment of the present invention.

Turning now to FIG. 10, a meter 410 is illustrated that may be used in combination with the present invention. The meter 410 comprises a housing 412, a testing mechanism 414 including a sensor opening 416, a display 418, and a button set 420. The housing 412 includes a first end 412*a* and an opposing second end 412*b*. The housing 412 further includes a plurality of wall portions 412*c-f* located between, and generally perpendicular to, the first and second ends 412*a-b*. According to one embodiment, the display 418 and button set 420 are located on the first end 412*a* of the housing 412 while an auto-calibration feature 426 (FIG. 12*a*) is located on the second end 412*b* of the housing 412. In the illustrated embodiment, the testing mechanism 414 is located on the first wall 412*c* along with a sensor-container opening 422. The sensor-container opening 422 is adapted to seat a sensor container 460 (FIG. 11) therein.

The sensor-container opening 422 forms a cavity between the third wall 412*e* and the fourth wall 412*f* of the housing 412. In the illustrated embodiment, both the third wall 412*e* and the fourth wall 412*f* include respective extensions 424*a*, 424*b* projecting therefrom. The extensions 424*a*, 424*b* are adapted to seat a portion of the sensor container 460 (FIG. 11) thereon and allow an auto-calibration feature 426 (FIG. 12*a*) to contact a calibration label 464 located on the sensor container 460.

Figure 11:
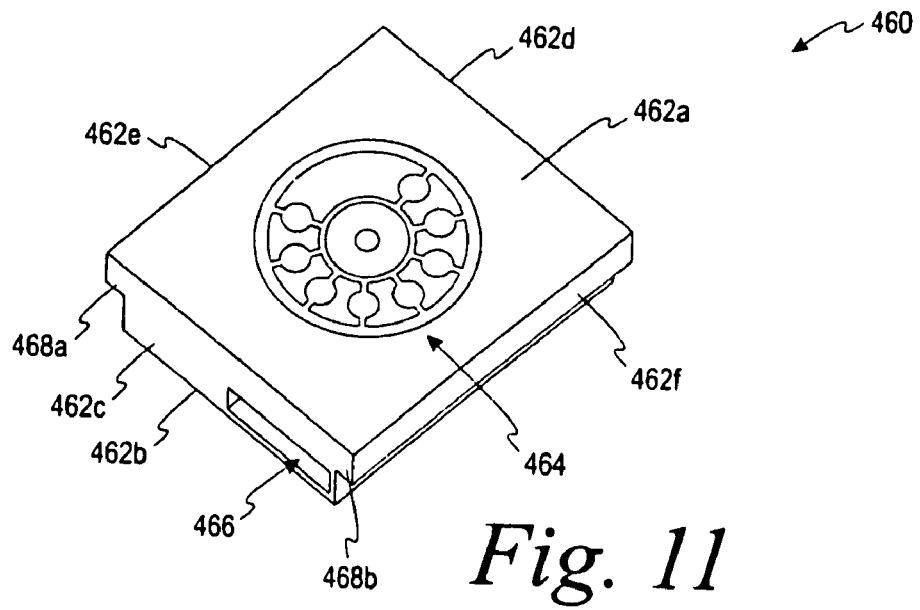
FIG. 11 is a perspective view of a sensor container adapted to be seated on the meter of FIG. 10, according to one embodiment.

Referring also to FIG. 11, a sensor container 460 is illustrated that may be used in combination with the meter 410 of FIG. 10. The sensor container 460 includes a housing 462 adapted to enclose a plurality of test sensors (e.g., test sensor 38 illustrated in FIGS. 3-4). The housing includes a first end 462*a* and an opposing second end 462*b*. The housing further includes a plurality of wall portions 462*c-f* located between, and generally perpendicular to, the first and second ends 462*a-b*. According to one embodiment, a calibration label 464 is located on the first end 462*a* of the sensor container 460.

Figure 12A:
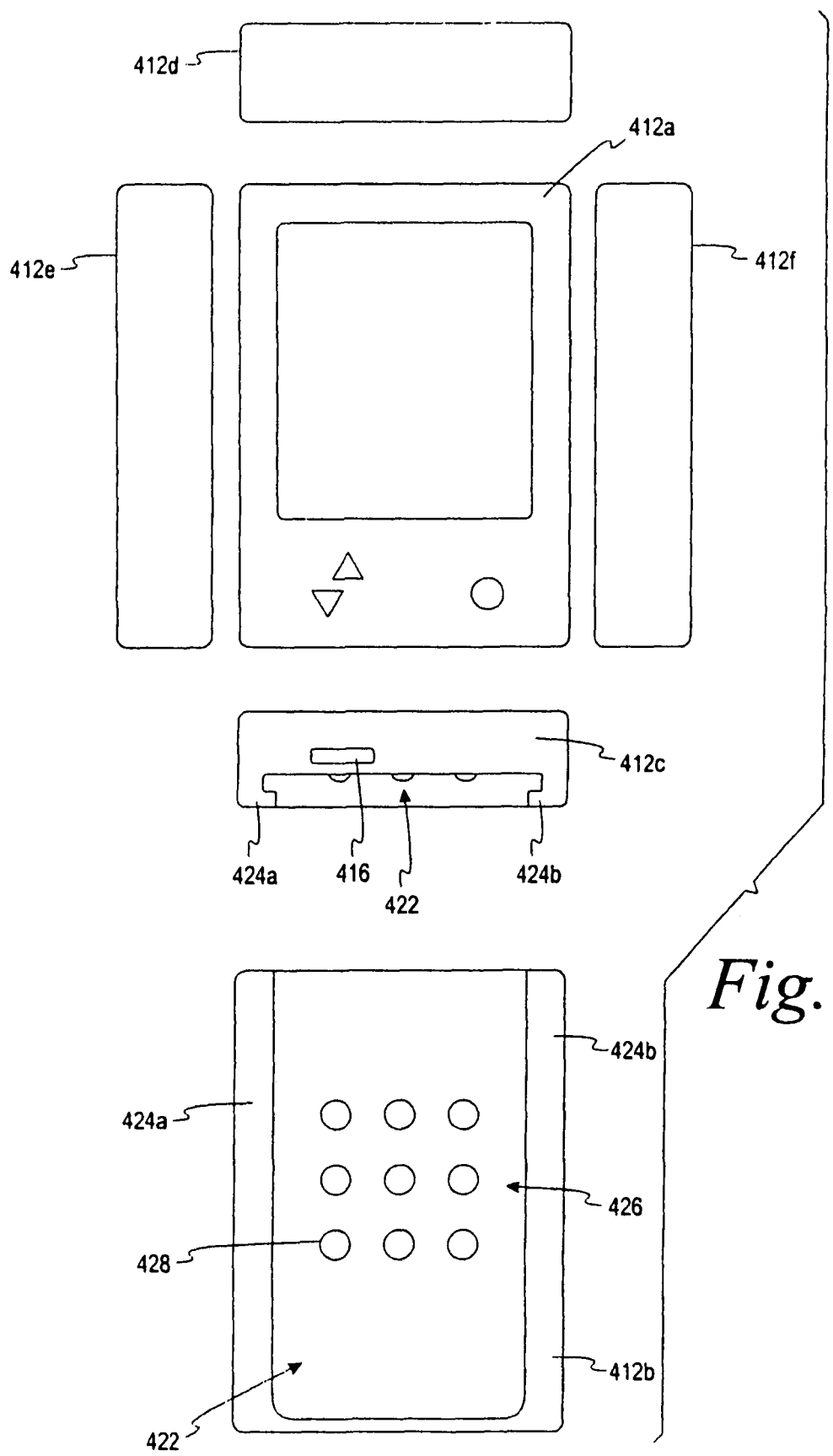
FIG. 12a is a layout view of the meter of FIG. 10.
Figure 12B:
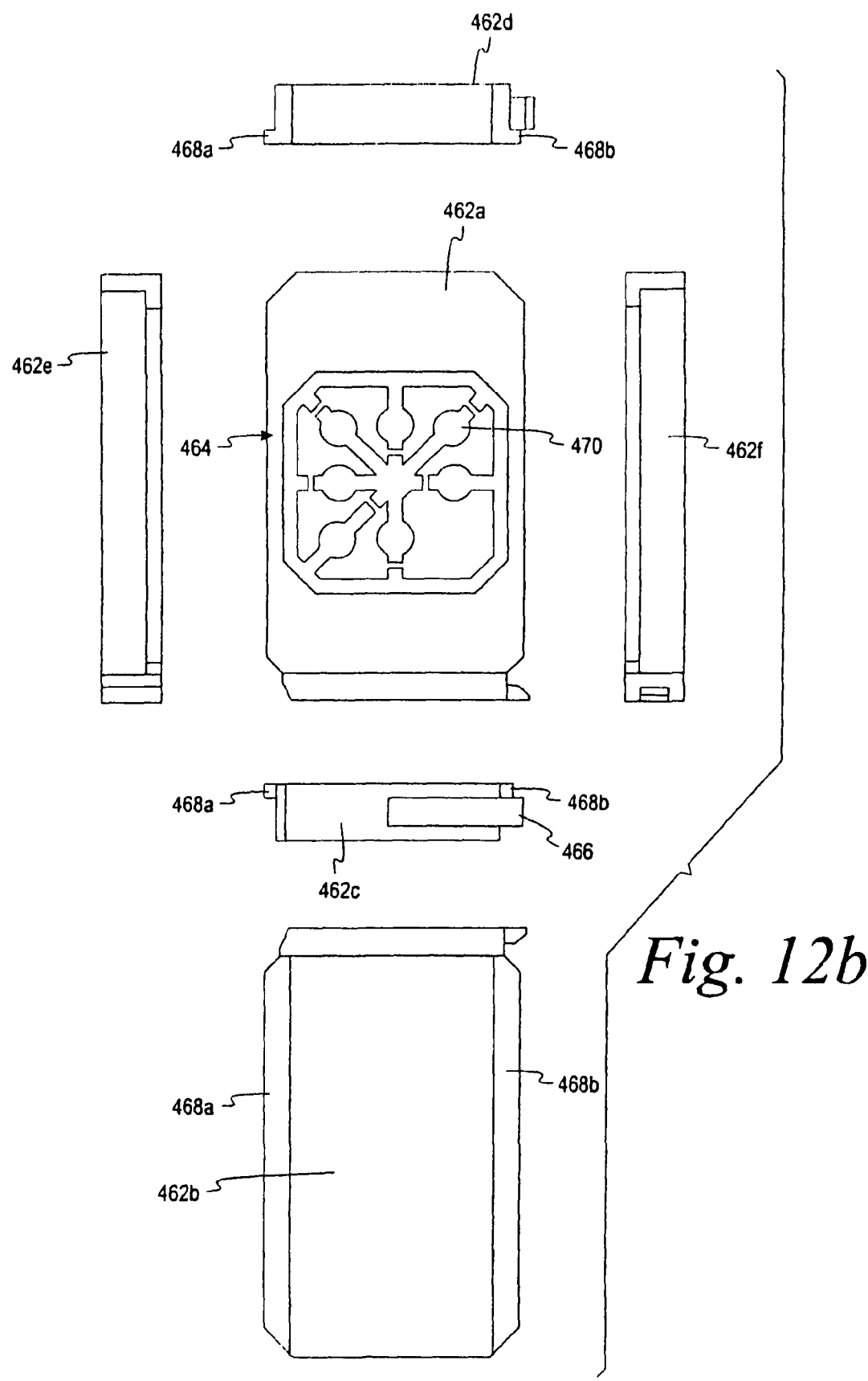
FIG. 12b is a layout view of the sensor cartridge of FIG. 11.
Figure 12C:
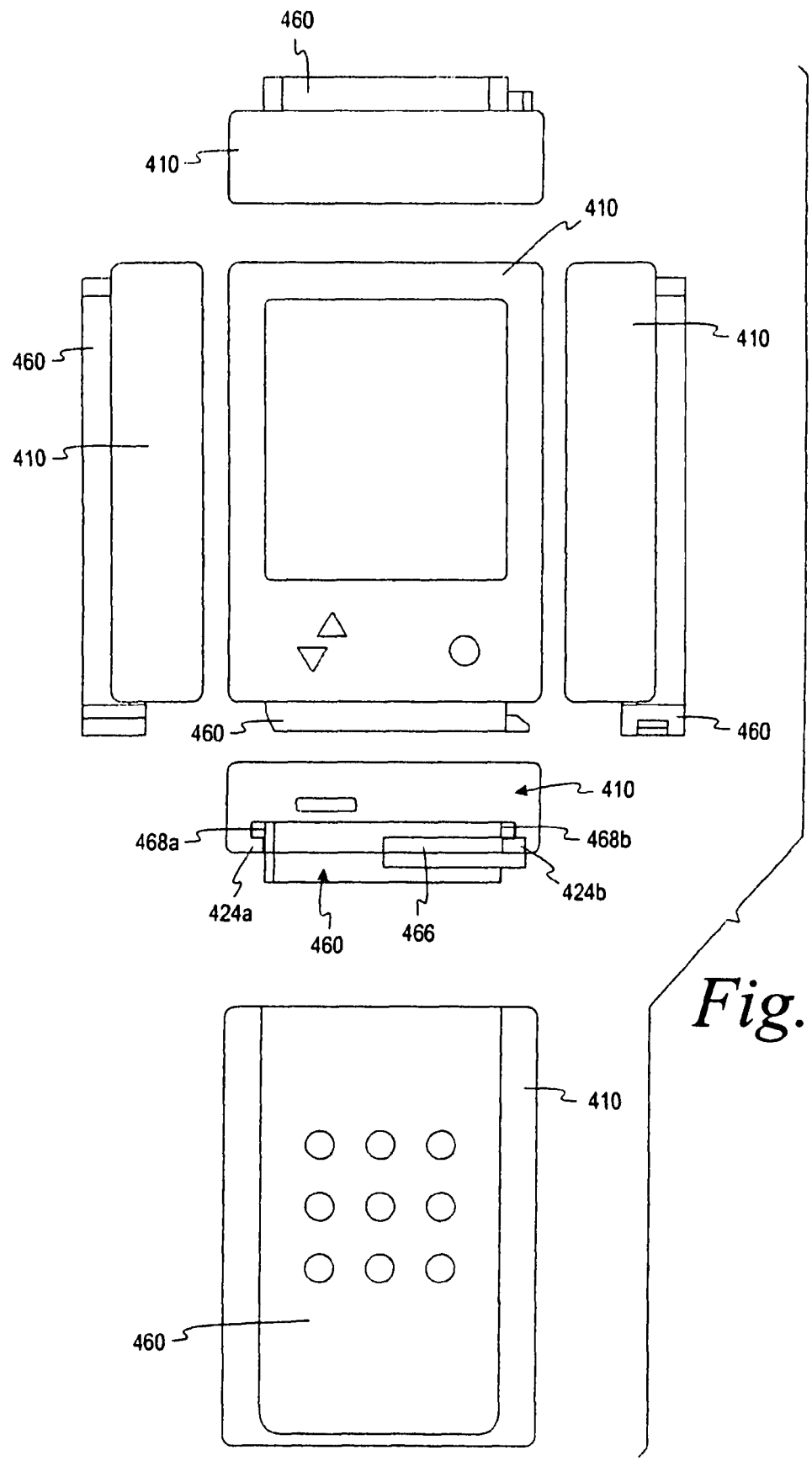
FIG. 12c is a layout view of the sensor cartridge of FIG. 11 seated on the meter of FIG. 10.

The sensor container 460 includes a sensor aperture 466 adapted to allow at least one of the plurality of test sensors to be removed from the sensor container 460. The sensor container 460, according to one embodiment, includes a plurality of wings 468*a*, 468*b* extending from the third wall 462*e* and the fourth wall 462*f* of the sensor container 460, respectively. The wings 468*a*, 468*b* are adapted to allow the sensor container 460 to be seated on the meter 410 such that the calibration label 464 located on the sensor container 460 is contacted to the auto-calibration feature 426 (FIG. 12*a*) of the meter 410. Referring now to FIGS. 12*a-c*, the seating of the sensor container 460 on the meter 410 will be illustrated, according to one embodiment. The sensor container 460 is seated on the meter 410 so as to bring a plurality of electrical contacts 470 provided on the calibration label 464 into contact with a plurality of calibration contacts 428 provided with the auto-calibration feature 426. By contacting the plurality of electrical contacts 470 with the plurality of calibration contacts 428, the auto-calibration information contained on the calibration label 464 can be read by the meter 410 to calibrate the meter 410 to accurately test a fluid sample applied to a test sensor.

The sensor container 460 is seated on the meter 410, in one embodiment, by sliding the first end 462*a* of the sensor container 460 into the sensor-container opening 422 formed in the meter 410. The sensor container 460 is inserted into the sensor-container opening 422 such that the wings 468*a-b* of the sensor container 460 are seated on the respective extensions 424*a-b* of the third and fourth walls 412*e-f* of the meter 410. As illustrated in FIG. 12*c*, when the sensor container 460 is seated on the meter 410, the sensor aperture 466 remains externally accessible by a user to allow a test sensor to be removed from the sensor container 460 by a user. The test sensor can then be inserted by the user into the sensor opening 416 and the calibration information read by the meter 410 from the calibration label 464 located on the sensor container 460 can be used to calibrate the meter 410 for a fluid sample analysis.

Turning now to FIGS. 13*a-d*, the seating of a sensor container 560 on a meter 510 will be illustrated, according to other embodiments of the present invention. The meter 510 includes a first end 512*a* and an opposing second end 512*b*. The meter 510 further includes a plurality of wall portions 512*c-f* located between, and generally perpendicular to, the first and second ends 512*a-b*. According to one embodiment, an auto-calibration feature 526 is located on the second end 512*b* of the meter 510. In the illustrated embodiment, a first sensor-container opening 522*a* is located on the first wall 512*c* and a second sensor-container opening 522*b* is located on the second wall 512*d*.

The first and second sensor-container openings 522*a-b* are adapted to seat the sensor container 560 therein. Both the first and second sensor-container opening 522*a-b* form a cavity between the third wall 512*e* and the fourth wall 512*f* of the meter 510. In the illustrated embodiment, both the third wall 512*e* and the fourth wall 512*f* include extensions 524*a*, 524*c* and 524*b*, 524*d* located on opposite ends of the respective walls. The extensions 424a-d are adapted to seat a portion of the sensor container 560 thereon and allow the auto-calibration feature 526 to contact a calibration label 564 located on the sensor container 560.

The sensor container 560 includes a housing adapted to enclose a plurality of test sensors (e.g., test sensor 38 illustrated in FIGS. 3-4). The housing includes a first end 562a and an opposing second end 562b. The housing further includes a plurality of wall portions 562c-f located between, and generally perpendicular to, the first and second ends 562a-b. According to one embodiment, the calibration label 564 is located on the first end 562a of the sensor container 560.

The sensor container 560 includes a sensor aperture 566 adapted to allow at least one of the plurality of test sensors to be removed from the sensor container 560. The sensor container 560, according to one embodiment, includes a plurality of wings 568a, 568b extending from the third wall 562e and the fourth wall 562f of the sensor container 560, respectively. The wings 568a, 568b are adapted to allow the sensor container 560 to be seated on the meter 510 such that the calibration label 564 located on the sensor container 560 is contacted to the auto-calibration feature 526 of the meter 510. In the illustrated embodiment, the wings 568a, 568b only partially extend along the length of the third wall 562e and the fourth wall 562f, as will be discussed further below.

Figure 13B:
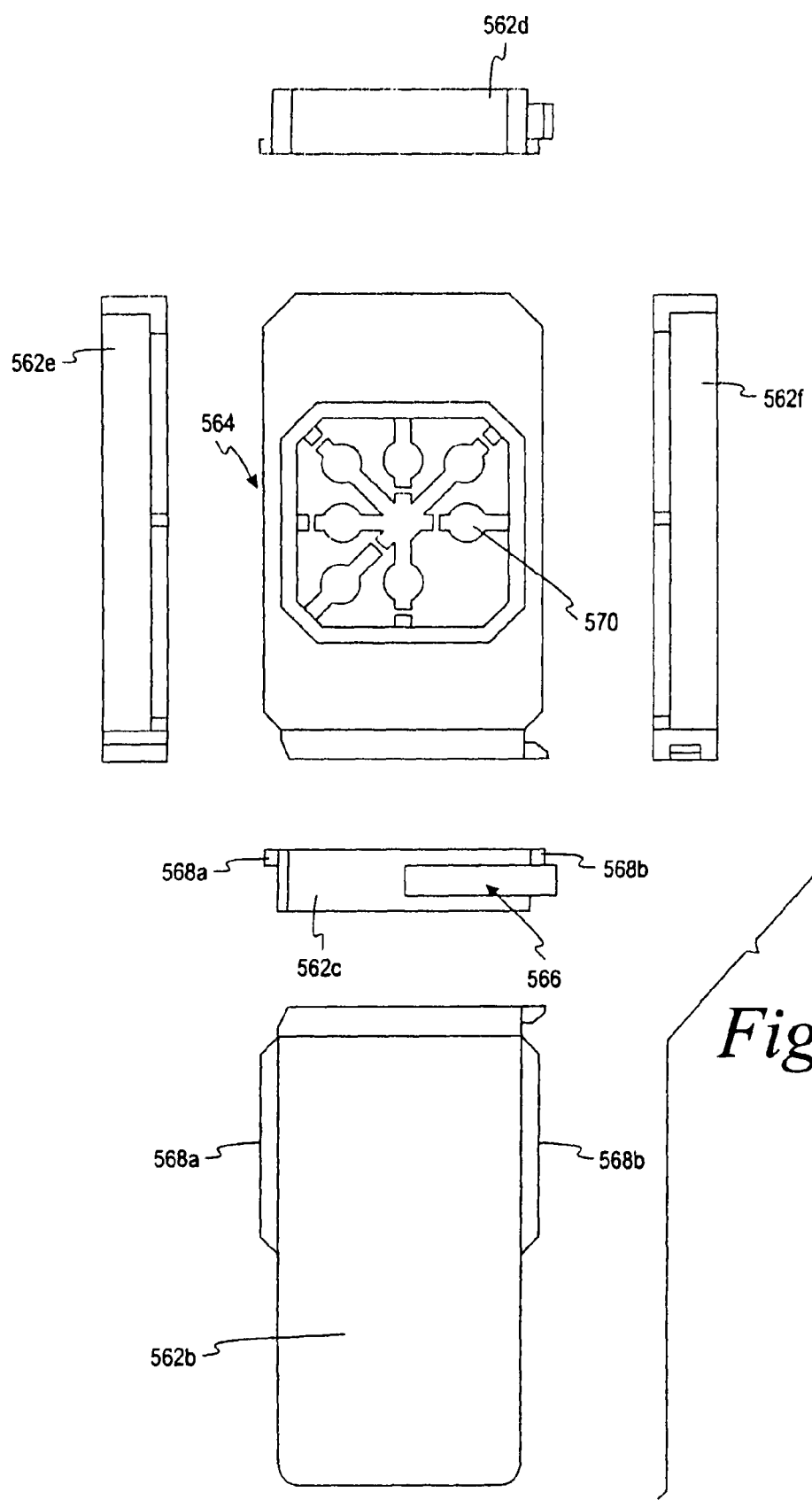
FIG. 13b is a layout view of a sensor container adapted to be seated on the meter of FIG. 13a, according to another embodiment of the present invention.
Figure 13C:
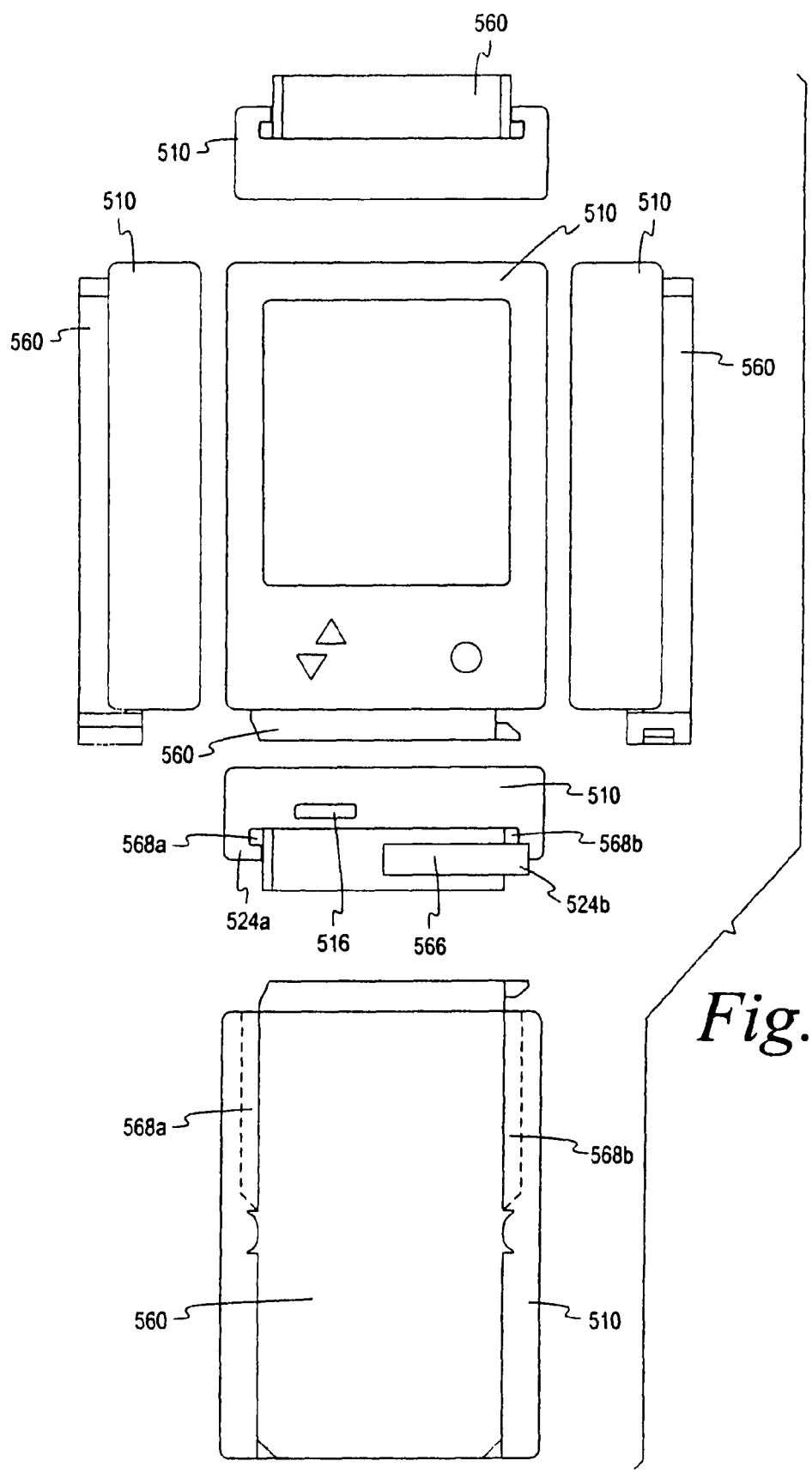
Figure 13D:
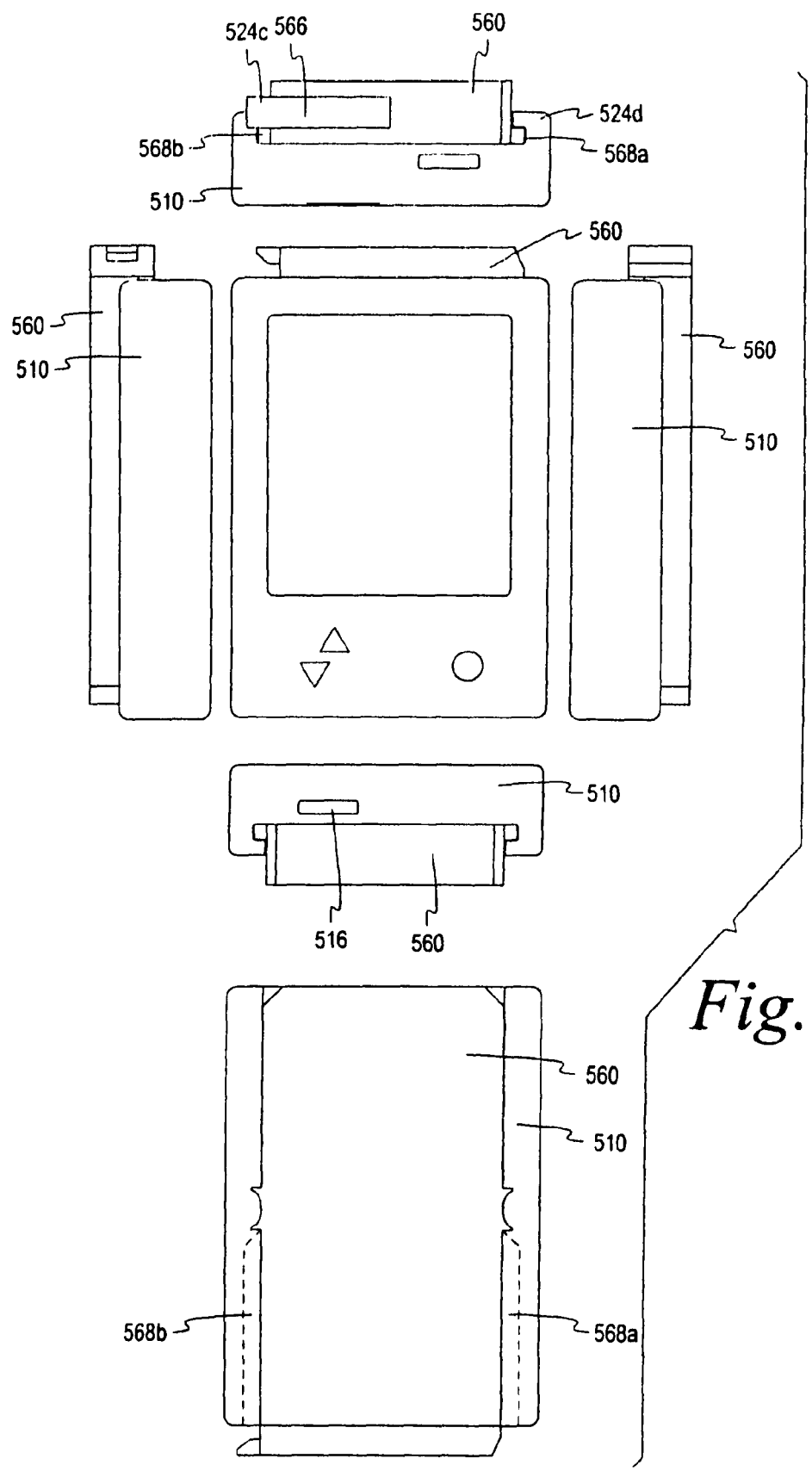

As best illustrated in FIGS. 13c-d, the various seating orientations of the sensor container 560 on the meter 510 will be described, according to some embodiments of the present invention. The sensor container 560 is seated on the meter 510 so as to bring a plurality of electrical contacts 570 provided on the calibration label 564 into contact with a plurality of calibration contacts 528 provided with the auto-calibration feature 526. By contacting the plurality of electrical contacts 570 with the plurality of calibration contacts 528, the auto-calibration information contained on the calibration label 564 can be read by the meter 510 to calibrate the meter 510 to accurately test a fluid sample applied to a test sensor.

The sensor container 560 is seated on the meter 510, in one embodiment, by sliding the first end 562a of the sensor container 560 into the first sensor-container opening 522a formed in the first wall 512c of the meter 510. The sensor container 560 is inserted into the first sensor-container opening 522a such that the wings 568a-b of the sensor container 560 are seated on the respective extensions 524a-b of the third and fourth walls 512e-f of the meter 510. The sensor container 560 continues to be inserted into the first sensor-container opening 522a until the wings 568a-b of the sensor container 560 engage one or more mechanical stops 530a-b (as best illustrated in FIG. 13b) located along the extensions 524. Because the wings 568a-b only partially extend along the length of the third wall 562e and the fourth wall 562f of the sensor container, a substantial portion of the sensor container 560 is partially enclosed within the first and second sensor-openings 522a-b when the wings 568a-b engage the mechanical stops 530a-b. When the sensor container 560 is seated in this embodiment, the sensor aperture 566 is located proximate the sensor opening 516 of the meter 510.

Alternatively, in another embodiment, the sensor container 560 may be seated on the meter 510 by sliding the first end 562a of the sensor container 560 into the second sensor-container opening 522b formed in the second wall 512d of the meter 510. The sensor container 560 is inserted into the second sensor-container opening 522b such that the wings 568a-b of the sensor container 560 are seated on the respective extensions 524c-d of the third and fourth walls 512e-f of the meter 510. The sensor container 560 continues to be inserted into the second sensor-container opening 522b until the wings 568a-b of the sensor container 560 engage one or more mechanical stops 530a-b (as best illustrated in FIG. 13b) located along the extensions 524. As discussed above, a substantial portion of the sensor container 560 is partially enclosed within both the first and second sensor-openings 522a-b when the wings 568a-b engage the mechanical stops 530a-b. However, when the sensor container 560 is seated in this embodiment, the sensor aperture 566 is opposite the sensor opening 516 of the meter 510.

As illustrated in FIGS. 13c-d, when the sensor container 560 is seated on the meter 510, the sensor aperture 566 remains externally accessible by a user to allow a test sensor to be removed from the sensor container 560 by a user. The test sensor can then be inserted by the user into the sensor opening 516 and the calibration information read by the meter 510 from the calibration label 564 located on the sensor container 560 can be used to calibrate the meter 510 for a fluid sample analysis.

Figure 14:
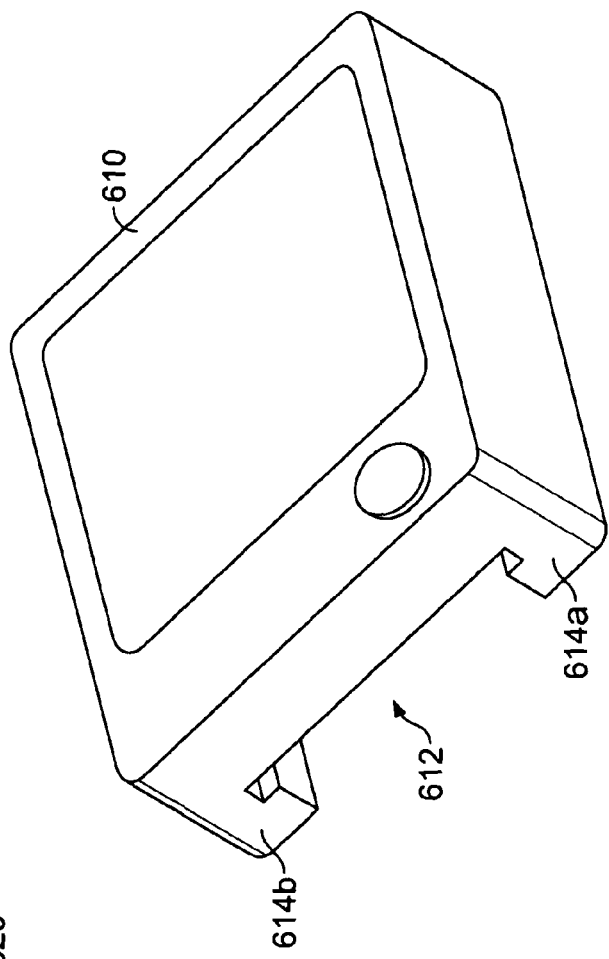
FIG. 14 is a perspective view of a meter adapted to seat a sensor container, according to another embodiment of the present invention.
Figure 15:
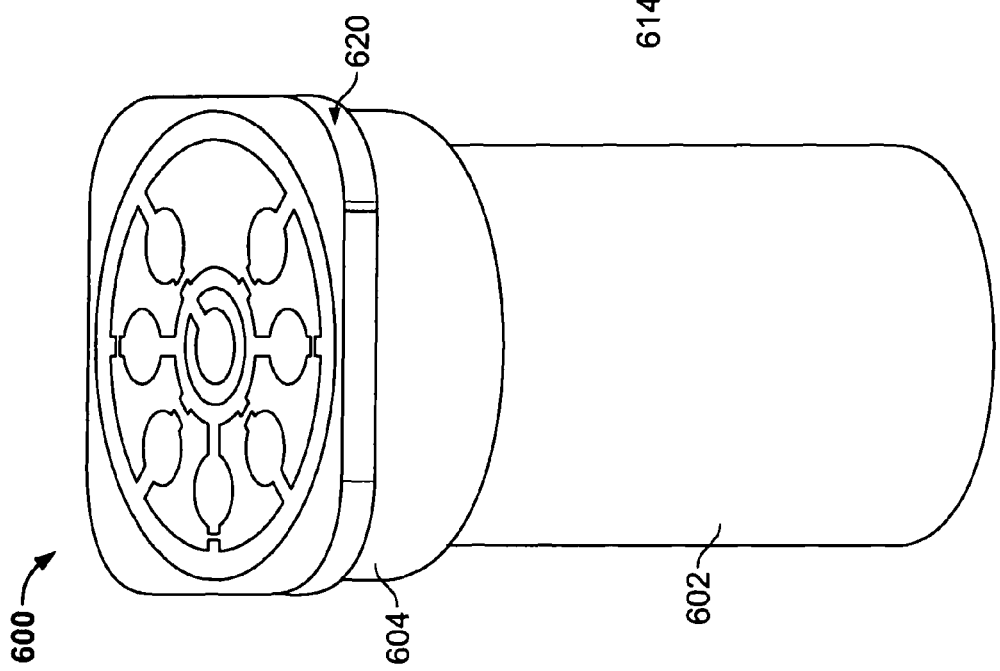
FIG. 15 is a perspective view of a sensor container adapted to be seated on the meter of FIG. 14, according to one embodiment.

Turning now to FIGS. 14-15, a meter 610 and a sensor container 600 are illustrated, according to yet another embodiment of the present invention. The meter 610 includes a sensor-container opening 612 that is adapted to allow a portion of the sensor container 600 to be inserted therein. A plurality of extensions 614a-b is formed on the meter 610 and is adapted to engage wings 620, or a slot, formed on a lid 604 of the sensor container 600. In the illustrated embodiment, the wings 620 allow a base 602 of the sensor container 600 to be removed from the lid 604 when the sensor container 600 is partially inserted into the sensor-container opening 612. In alternative embodiments, the wings 620 or a slot may be placed on the base 602 of the sensor container 600 so as to require a user to remove a test sensor from the sensor container 600 prior to inserting a portion of the sensor container 600 into the sensor-container opening 612.

In still other embodiments, the lid 104 of the sensor container 100 (FIG. 5) may be inserted into the sensor-container opening 612. Because the lid 104 of the sensor container 100 has larger diameter than the base 102, as illustrated in FIG. 5, the extensions 614a-b are capable of supporting the sensor container 100 in the meter 610 without a slot being provided in the sensor container 100.

Figure 16:
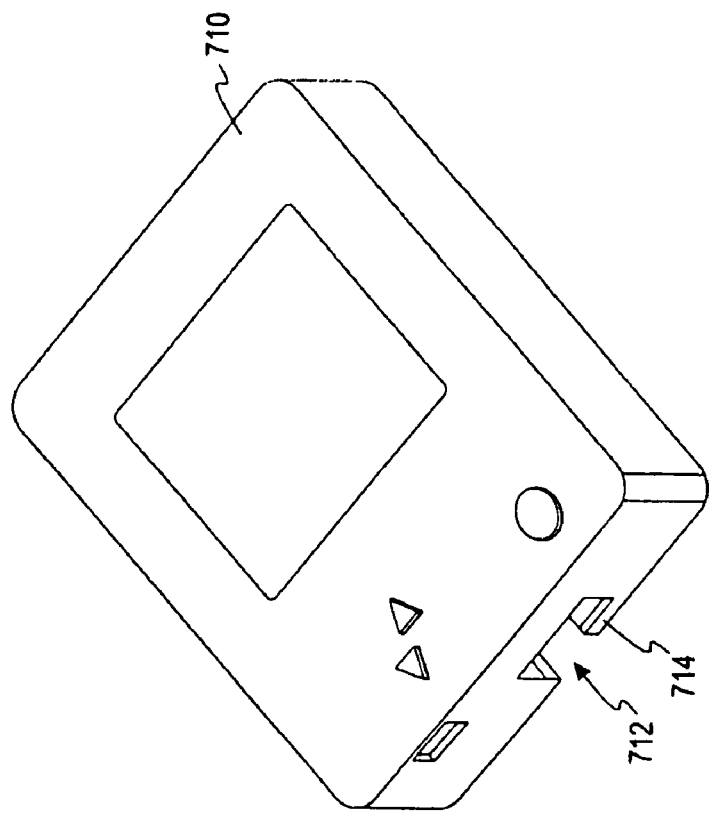
FIG. 16 is a perspective view of a meter adapted to seat a sensor container, according to yet another embodiment of the present invention.
Figure 17:
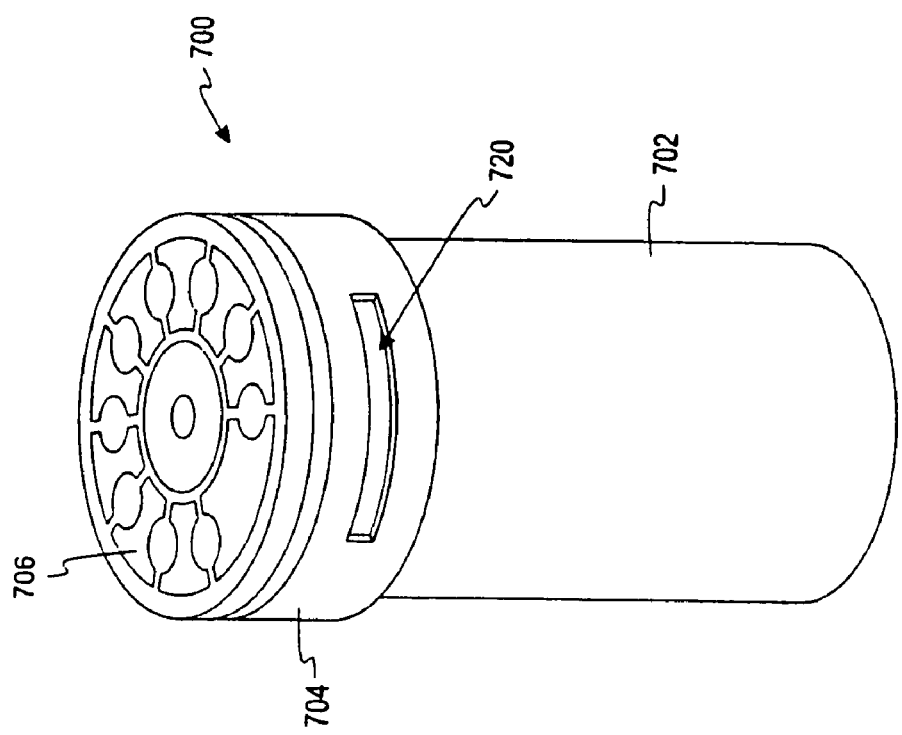
FIG. 17 is a perspective view of a sensor container adapted to be seated on the meter of FIG. 16, according to one embodiment.

Turning now to FIGS. 16-17, a meter 710 and a sensor container 700 are illustrated, according to still another embodiment of the present invention. The meter 710 includes a sensor-container opening 712 that is adapted to allow a portion of the sensor container 700 to be inserted therein. An extension 714a-b is formed on the meter 710 and is adapted to engage a notch 720 formed on a lid 704 of the sensor container 700. In the illustrated embodiment, the notch 720 allows a base 702 of the sensor container 600 to be removed from the lid 704 when the sensor container 700 is partially inserted into the sensor-container opening 712. In alternative embodiments, the notch 720 may be placed on the base 702 of the sensor container 700 so as to require a user to remove a test sensor from the sensor container 700 prior to inserting a portion of the sensor container 700 into the sensor-container opening 712.

The utilization of a notch 720 on only one portion of the sensor container 700 facilitates the proper orientation of a calibration label 706 with a auto-calibration feature (not shown) located within the sensor-container opening 712 of the meter 710. As such, the notch 720 may be utilized when a single and particular orientation of the calibration label 706 is desired or required.

As can be seen from the above-described embodiments, the encoded calibration information contained on the calibration labels can be read and determined by the integrated meter directly from the sensor container, without inserting the sensor container into the integrated meter. Thus, the above-described apparatuses allow the integrated meter to automatically determine the calibration information for a test sensor contained within a sensor container, where the sensor container is adapted to allow a user to individually remove the test sensor from the sensor container and insert the removed test sensor into the integrated meter.

The integrated meter is capable of automatically determining the calibration information for the inserted test sensor without requiring the user to key in the calibration information or locate and insert a calibration chip or other device into the integrated meter. Because the sensor container includes the calibration label directly thereon, when the user opens the sensor container to remove a test sensor, the user necessarily has the calibration label. The integrated meter is designed, in some embodiments, to require that a user contact the calibration label to the auto-calibration feature before a fluid sample can be analyzed, but after the test sensor has been inserted into the integrated meter. This can help to ensure that the proper calibration information is provided for the particular test strip being inserted into the integrated meter.

As described above, the sensing contact is an electrical contact and continuity between the sensing contact and any other calibration contact can be used to establish that contact has been established between the label and the auto-calibration feature. An alternate approach, not using a contact on the label, is for the instrument to instead have a pushbutton-like switch that activates when mechanical contact is established by the container with the auto-calibration feature. For either implementation, the microcontroller would repeatedly attempt to read the label until a valid calibration code is detected or, through the sensing mechanism, it is determined that the label has been withdrawn.

The above implementation has the test-sensor container snap onto, or otherwise attach to, the outside of the instrument (or the instrument attach to the bottle) with the label contacting the calibration feature. It could then remain connected until all sensors are consumed and the old bottle replaced with a new one. Not only would this integrate sensor storage with the instrument, it would reduce the chance of a tester not contacting the label to the calibration feature prior to running a test from a new bottle with different calibration code than the last. An alternate implementation would be to have the calibration label momentarily brought in contact with the calibration feature. Once the microcontroller has transferred the calibration information, the label can be withdrawn with the meter remembering and using the transferred information.

Alternative Embodiment A

A test system for determining an analyte concentration in a fluid sample, comprising:
a sensor container having a base and a lid, the sensor container being adapted to enclose a plurality of test sensors therein, the sensor container including a calibration label attached thereto, the calibration label including a plurality of electrical contacts located thereon, the electrical contacts being adapted to encode calibration information onto the calibration label; and
a testing device having a sensor-container opening formed thereon, the sensor-container opening having an auto-calibration feature located therein, the auto-calibration feature being external to the testing device, the auto-calibration feature including a plurality of calibration elements being adapted to communicate with the plurality of electrical contacts on the calibration label,
wherein the testing device is adapted to determine the calibration information encoded on the calibration label in response to the calibration elements engaging the electrical contacts, a portion of the sensor container remaining external to the meter while the encoded calibration information is being determined.

Alternative Embodiment B

The test system of Alternative Embodiment A, wherein the calibration label is attached to the lid of the sensor container.

Alternative Embodiment C

The test system of Alternative Embodiment A, wherein the testing device and the auto-calibration feature form a digital electronic circuit.

Alternative Embodiment D

The test system of Alternative Embodiment A, wherein the testing device and the auto-calibration feature form an analog electronic circuit.

Alternative Embodiment E

The test system of Alternative Embodiment A, wherein the calibration elements are calibration pins extending from the auto-calibration feature.

Alternative Embodiment F

The test system of Alternative Embodiment A, wherein the testing device includes at least one extension.

Alternative Embodiment G

The test system of Alternative Embodiment F, wherein the sensor container includes a slot adapted to be engaged by the at least one extension.

Alternative Embodiment H

The test system of Alternative Embodiment G, wherein the sensor container includes at least one notch adapted to be engaged by the at least one extension.

Alternative Embodiment I

The test system of Alternative Embodiment G, wherein the sensor container includes at least one wing adapted to be seated on the at least one extension.

Alternative Embodiment J

The test system of Alternative Embodiment A, wherein the testing device includes at least two sensor-container openings.

Alternative Embodiment K

A test system for determining an analyte concentration in a fluid sample, comprising:
a sensor container having a base and a lid, the sensor container including a calibration label attached thereto, the calibration label including a plurality of electrical contacts located thereon, a first one of the plurality of electrical contacts being connected via a conductive trace to a first ring, a second one of the plurality of electrical contacts being connected via a conductive trace to a second ring, and a third one of the plurality of electrical contacts being disconnected from both the first and second ring, the calibration information being encoded onto the calibration label based on the connections and disconnections of the electrical contacts with the first and second ring; and a testing device having a microprocessor internally located therein and a sensor-container opening formed thereon, the sensor-container opening having an auto-calibration feature located therein, the auto-calibration feature being external to the testing device, the auto-calibration feature including a plurality of calibration elements being adapted to communicate with the plurality of electrical contacts on the calibration label, the microprocessor being adapted to determine the calibration information encoded on the calibration label in response to the plurality of electrical contacts engaging the plurality of calibration elements external to the testing device.

Alternative Embodiment L

The test system of Alternative Embodiment K, wherein the testing device further includes a memory device located therein, the memory device being in communication with the microprocessor, the memory device being adapted to store lookup tables for predefined calibration codes thereon.

Alternative Embodiment M

The test system of Alternative Embodiment K, wherein the testing device and the auto-calibration feature form a digital electronic circuit.

Alternative Embodiment N

The test system of Alternative Embodiment K, wherein the testing device and the auto-calibration feature form an analog electronic circuit.

Alternative Embodiment O

The test system of Alternative Embodiment K, wherein the plurality of calibration elements is calibration pins extending from the auto-calibration feature.

Alternative Embodiment P

The test system of Alternative Embodiment K, wherein the calibration label includes a sensing contact, the plurality of electrical contacts being generally located around the sensing contact, the sensing contact being adapted to be engaged by a sensing pin formed on the auto-calibration feature, the sensing contact and the sensing pin being adapted to inform the microprocessor that the plurality of calibration elements are being engaged with the plurality of electrical contacts.

Alternative Embodiment Q

The test system of Alternative Embodiment K, wherein the testing device is an integrated meter.

Alternative Embodiment R

The test system of Alternative Embodiment K, wherein the third one of the plurality of electrical contacts indicates an index position for the calibration label.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

What is claimed is:

1. A test system for determining an analyte concentration in a fluid sample, comprising:

a sensor container having a base and a lid, the sensor container enclosing a plurality of test sensors therein being accessible via the lid, the sensor container including a calibration label attached thereto, the calibration label including a plurality of electrical contacts located thereon, the electrical contacts being adapted to encode calibration information onto the calibration label; and a testing device including a housing with an exterior surface, the exterior surface of the housing defining a sensor-container opening, the sensor-container opening enabling accessibility of an auto-calibration feature, the auto-calibration feature being external to the exterior surface of the housing, the auto-calibration feature including a plurality of calibration elements being adapted to communicate with the plurality of electrical contacts on the calibration label, wherein the testing device is adapted to determine the calibration information encoded on the calibration label in response to the calibration elements engaging the electrical contacts, a portion of the sensor container remaining external to the testing device while the encoded calibration information is being determined.

2. The test system of claim 1, wherein the calibration label is attached to the lid of the sensor container.

3. The test system of claim 1, wherein the testing device and the auto-calibration feature form a digital electronic circuit.

4. The test system of claim 1, wherein the testing device and the auto-calibration feature form an analog electronic circuit.

5. The test system of claim 1, wherein the calibration elements are calibration pins extending from the auto-calibration feature.

6. The test system of claim 1, wherein the testing device includes at least one extension.

7. The test system of claim 6, wherein the sensor container includes a slot adapted to be engaged by the at least one extension.

8. The test system of claim 7, wherein the sensor container includes at least one notch adapted to be engaged by the at least one extension.

9. The test system of claim 7, wherein the sensor container includes at least one wing adapted to be seated on the at least one extension.

10. The test system of claim 1, wherein the testing device includes at least two sensor-container openings.

11. A test system for determining an analyte concentration in a fluid sample, comprising:

a sensor container having a base and a lid, the sensor container including a calibration label attached thereto, the calibration label including a plurality of electrical contacts located thereon, a first one of the plurality of electrical contacts being connected via a conductive trace to a first ring, a second one of the plurality of electrical contacts being connected via a conductive trace to a second ring, and a third one of the plurality of electrical contacts being disconnected from both the first and second ring, the calibration information being encoded onto the calibration label based on the connections and disconnections of the electrical contacts with the first and second ring; and a testing device having a microprocessor internally located therein and including a housing with an exterior surface, the exterior surface of the housing defining a sensor-container opening, the sensor-container opening enabling accessibility of an auto-calibration feature, the auto-calibration feature being external to the exterior surface of the housing, the auto-calibration feature including a plurality of calibration elements being adapted to communicate with the plurality of electrical contacts on the calibration label, the microprocessor being adapted to determine the calibration information encoded on the calibration label in response to the plurality of electrical contacts engaging the plurality of calibration elements external to the testing device.

12. The test system of claim 11, wherein the testing device further includes a memory device located therein, the memory device being in communication with the microprocessor, the memory device being adapted to store lookup tables for predefined calibration codes thereon.

13. The test system of claim 11, wherein the testing device and the auto-calibration feature form a digital electronic circuit.

14. The test system of claim 11, wherein the testing device and the auto-calibration feature form an analog electronic circuit.

15. The test system of claim 11, wherein the plurality of calibration elements is calibration pins extending from the auto-calibration feature.

16. The test system of claim 11, wherein the calibration label includes a sensing contact, the plurality of electrical contacts being generally located around the sensing contact, the sensing contact being adapted to be engaged by a sensing pin formed on the auto-calibration feature, the sensing contact and the sensing pin being adapted to inform the microprocessor that the plurality of calibration elements are being engaged with the plurality of electrical contacts.

17. The test system of claim 11, wherein the testing device is an integrated meter.

18. The test system of claim 11, wherein the third one of the plurality of electrical contacts indicates an index position for the calibration label.

19. A test system for determining an analyte concentration in a fluid sample, comprising:

a sensor container having a base and a lid, the sensor container enclosing a plurality of test sensors therein, the sensor container including a calibration label attached thereto, the calibration label including a plurality of electrical contacts located thereon, the electrical contacts being adapted to encode calibration information onto the calibration label; and a testing device including a housing with an exterior surface, the housing includes a plurality of walls that extends outwardly from the remainder of the housing and assist in defining a sensor-container opening, the sensor-container opening enabling accessibility of a calibrating feature located on the exterior surface of the housing, the calibrating feature including a plurality of calibration elements being adapted to communicate with the plurality of electrical contacts on the calibration label, wherein the testing device is adapted to determine the calibration information encoded on the calibration label in response to the calibration elements engaging the electrical contacts, a portion of the sensor container remaining external to the testing device while the encoded calibration information is being determined.

20. The test system of claim 19, wherein the housing has a first end and a second end and wherein at least a portion of the plurality of walls is generally perpendicular to the first and second ends.

21. The test system of claim 20, wherein the calibration label is attached to the lid of the sensor container.

22. A test system for determining an analyte concentration in a fluid sample, comprising:

a sensor container having a base and a lid, the sensor container enclosing a plurality of test sensors therein being accessible via the lid, the sensor container including a calibration label attached thereto, the calibration label including a plurality of electrical contacts located thereon, the electrical contacts being adapted to encode calibration information onto the calibration label; and a testing device including a housing with an exterior surface, the housing including a plurality of extensions that assist in defining a sensor-container opening, the sensor-container opening enabling accessibility of a calibrating feature, the calibrating feature being external to the exterior surface of the housing, the calibrating feature including a plurality of calibration elements being adapted to communicate with the plurality of electrical contacts on the calibration label, wherein the testing device is adapted to determine the calibration information encoded on the calibration label in response to the calibration elements engaging the electrical contacts, a portion of the sensor container remaining external to the testing device while the encoded calibration information is being determined.

* * * * *